United States Patent
Miller et al.

(10) Patent No.: US 11,450,434 B2
(45) Date of Patent: Sep. 20, 2022

(54) IMPLEMENTATION OF MACHINE-LEARNING BASED QUERY CONSTRUCTION AND PATTERN IDENTIFICATION THROUGH VISUALIZATION IN USER INTERFACES

(71) Applicant: HVH Precision Analytics LLC, Wayne, PA (US)

(72) Inventors: Chris Miller, Wayne, PA (US); Tyler Folta, Wayne, PA (US); Tara Grabowsky, Bryn Mawr, PA (US); Oodaye Shukla, Wayne, PA (US)

(*) Notice: Subject to any disclaimer, the term of this patent is extended or adjusted under 35 U.S.C. 154(b) by 279 days.

(21) Appl. No.: 16/722,747

(22) Filed: Dec. 20, 2019

(65) Prior Publication Data

US 2020/0303071 A1    Sep. 24, 2020

Related U.S. Application Data

(60) Provisional application No. 62/783,155, filed on Dec. 20, 2018.

(51) Int. Cl.
*G16H 50/20* (2018.01)
*G16H 40/20* (2018.01)
(Continued)

(52) U.S. Cl.
CPC .............. *G16H 50/20* (2018.01); *G06F 17/18* (2013.01); *G16H 40/20* (2018.01); *G16H 50/70* (2018.01)

(58) Field of Classification Search
CPC ........ G06F 17/18; G16H 50/20; G16H 50/70; G16H 40/20
(Continued)

(56) References Cited

U.S. PATENT DOCUMENTS 8,068,993 B2    11/2011    Karlov et al.
8,655,695 B1 *   2/2014    Qu ..................... G06Q 30/0251
                                                                705/7.29
(Continued)

FOREIGN PATENT DOCUMENTS

CN        109147947 A  *  1/2019  ............. G16H 40/20
WO        WO2016094330    6/2016
WO        WO2018090009    5/2018

OTHER PUBLICATIONS

International Search Report and Written Opinion for International Application No. PCT/US2019/067893, dated Mar. 15, 2020, 8 pages.

*Primary Examiner* — John P Go
*Assistant Examiner* — Christopher B Wehrly
(74) *Attorney, Agent, or Firm* — Saul Ewing Arnstein & Lehr LLP

(57) ABSTRACT

A computer system, computer-implemented method, and computer program product include a processor(s) (executing code) that obtains a data set(s) related to a patient population diagnosed with a medical condition a database(s). The processor(s) identifies common features, generates patterns of the common features, and generates machine learning algorithms based on the patterns to identify presence or absence of the given medical condition in an undiagnosed patient. The processor(s) compiles a training set of data and tunes the machine learning algorithms with the training set of data. The processor(s) integrates the machine learning algorithms into a graphical user interface. The processor(s) obtains data related to the undiagnosed patient via the interface and applies the machine learning algorithms to determine a probability (numerical value indicating a percentage of commonality between the data related to the undiagnosed patient and the one or more patterns) and display the probability as a score in the interface.

20 Claims, 12 Drawing Sheets

(51) Int. Cl.
  *G16H 50/70* (2018.01)
  *G06F 17/18* (2006.01)
(58) Field of Classification Search
  USPC .......................................................... 705/2, 3
  See application file for complete search history.

(56) References Cited

U.S. PATENT DOCUMENTS

2017/0124269 A1* 5/2017 McNair .................. G16H 10/60
2019/0043618 A1* 2/2019 Vaughan ................ G16H 50/20
2019/0214141 A1* 7/2019 Chatterjee .............. G16H 50/20

* cited by examiner

200

Select ALS Score threshold for Does patient have prior history (9-21 months ago) of:

Threshold:
0.997

TPR/Sensitivity/Recall:
0.00163

TNR/Specificity:
1.00000

PPV/Precision:
1.00000

FPR:
0.0E+00

AUC:
0.74692

280

Symptoms/Diagnoses  270

| Item # | Description | Present |
|---|---|---|
| 1 | Dysarthria and anarthria | N |
| 2 | Other acquired deformities of ankle and foot | N |
| 3 | Cramp of limb\|Abnormal involuntary movements | N |
| 4 | Muscle weakness (generalized) | N |
| 5 | Other musculoskeletal symptoms referable to limbs\|Other symptoms involving nervous and musculoskeletal systems | N |
| 6 | Hereditary and idiopathic neuropathy, unspecified | N |
| 7 | Abnormality of gait | N |
| 8 | Disturbance of skin sensation | N |
| 9 | Displacement of cervical intervertebral disc without myelopathy | N |
| 10 | Thoracic or lumbosacral neuritis or radiculitis; unspecified | N |

Within past 9 months, does patient report:

Symptoms/Diagnoses  260

| Item # | Description | Present |
|---|---|---|
| 1 | Dysarthria and anarthria | N |
| 2 | Other acquired deformities of ankle and foot | N |
| 3 | Cramp of limb\|Abnormal involuntary movements | N |
| 4 | Muscle weakness (generalized) | N |
| 5 | Other musculoskeletal symptoms referable to limbs\|Other symptoms involving nervous and musculoskeletal systems | N |
| 6 | Hereditary and idiopathic neuropathy, unspecified | N |
| 7 | Abnormality of gait | N |
| 8 | Disturbance of skin sensation | N |
| 9 | Problems with voice production\|Other speech disturbance | N |
| 10 | Dysphagia; unspecified | N |
| 11 | Debility; unspecified\|Other malaise and fatigue | N |

ALS Score: 0.0000
Action: ALS Unlikely - No Action Needed

| Procedures | | |
|---|---|---|
| Item # | Description | Present |
| 1 | CPT Code 95886: Needle electromyography; each extremity; with related paraspinal areas; when performed; done with nerve conduction; amplitude and latency/velocity study; complete; five or more muscles studied; innervated by three or more nerves or four or more spinal levels (List separately in addition to code for primary procedure) | N |
| 2 | CPT Code 97001: Physical therapy evaluation | N |
| 3 | CPT Code 97110: Therapeutic procedure; 1 or more areas; each 15 minutes; therapeutic exercises to develop strength and endurance; range of motion and flexibility | N |
| 4 | CPT Code 95900: Nerve conduction, amplitude and latency/velocity study, each nerve; motor; without F-wave study | N |
| 5 | CPT Code 95903: Nerve conduction, amplitude and latency/velocity study, each nerve; motor; with F-wave study | N |
| 6 | CPT Code 95904: Nerve conduction, amplitude and latency/velocity study, each nerve; Sensory | N |
| 7 | CPT Code 72141: Magnetic resonance (eg; proton) imaging; spinal canal and contents; cervical; without contrast material | N |
| 8 | CPT Code 95860: Needle electromyography; 1 extremity with or without related paraspinal areas | N |
| 9 | CPT Code 95861: Needle electromyography; 2 extremities with or without related paraspinal areas | N |
| 10 | CPT Code 99213: Office or other outpatient visit for the evaluation and management of an established patient | N |

230

| Procedures | | |
|---|---|---|
| Item # | Description | Present |
| 1 | CPT Code 95886: Needle electromyography; each extremity; with related paraspinal areas; when performed; done with nerve conduction; amplitude and latency/velocity study; complete; five or more muscles studied; innervated by three or more nerves or four or more spinal levels (List separately in addition to code for primary procedure) | N |
| 2 | CPT Code 97001: Physical therapy evaluation | N |
| 3 | CPT Code 97110: Therapeutic procedure; 1 or more areas; each 15 minutes; therapeutic exercises to develop strength and endurance; range of motion and flexibility | N |
| 4 | CPT Code 95900: Nerve conduction, amplitude and latency/velocity study, each nerve; motor; without F-wave study | N |
| 5 | CPT Code 95903: Nerve conduction, amplitude and latency/velocity study, each nerve; motor; with F-wave study | N |
| 6 | CPT Code 95904: Nerve conduction, amplitude and latency/velocity study, each nerve; Sensory | N |
| 7 | CPT Code 72141: Magnetic resonance (eg; proton) imaging; spinal canal and contents; cervical; without contrast material | N |
| 8 | CPT Code 82607: Cyanocobalamin (Vitamin B-12); | N |
| 9 | CPT Code 70551: Magnetic resonance (eg; proton) imaging; brain (including brain stem); without contrast material | N |
| 10 | CPT Code 70553: Magnetic resonance (eg; proton) imaging; brain (including brain stem); without contrast material; followed by contrast material(s) and further sequences | N |
| 11 | CPT Code 72148: Magnetic resonance (eg; proton) imaging; spinal canal and contents; lumbar; without contrast material | N |

210

ALS Score: 0.0000
Action: ALS Unlikely - No Action Needed

| ALS Score: | 0.0000 |
| --- | --- |
| Action: | ALS Unlikely - No Action Needed |

210

Drugs 240

| Item # | Description | Present |
| --- | --- | --- |
| 1 | Pyridostigmine | N |
| 2 | Baclofen | N |
| 3 | Diazepam | N |
| 4 | Hydrocodone & Comb. | N |

Drugs 250

| Item # | Description | Present |
| --- | --- | --- |
| 1 | Pyridostigmine | N |
| 2 | Baclofen | N |
| 3 | Diazepam | N |
| 4 | Gabapentin | N |
| 5 | Fluoxetine | N |
| 6 | Memantine | N |
| 7 | Furosemide | N |

Select HAE Score threshold for referral:

Does patient have prior history of:

300

| Threshold: | |
|---|---|
| | 0.997 |
| TPR/Sensitivity/Recall: | |
| | 0.00407 |
| TNR/Specificity: | |
| | 1.00000 |
| PPV/Precision: | |
| | 1.00000 |
| FPR: | |
| | 0.0E+00 |
| AUC: | |
| | 0.74692 |

395

Symptoms/Diagnoses    320

| Item # | Description | Present |
|---|---|---|
| 1 | Allergic reactions | N |
| 2 | Swelling, mass, or lump In head and neck | N |
| 3 | Routine general medical examination at a healthcare facility | N |
| 4 | Immunizations and screening for infectious disease | N |
| 5 | Other screening for suspected conditions (not mental disorders or infectious disease) | N |
| 6 | Edema | N |
| 7 | Abdominal pain, unspecified site | N |
| 8 | Other upper respiratory disease | N |
| 9 | Unspecified symptom associated with female genital organs | N |
| 10 | Chronic vascular insufficiency of the intestine | N |

Within past year, does patient report:

Symptoms/Diagnoses    310

| Item # | Description | Present |
|---|---|---|
| 1 | Allergic reactions | N |
| 2 | Swelling, mass, or lump In head and neck | N |
| 3 | Routine general medical examination at a healthcare facility | N |
| 4 | Immunizations and screening for infectious disease | N |
| 5 | Other screening for suspected conditions (not mental disorders or infectious disease) | N |
| 6 | Edema | N |
| 7 | Abdominal pain, unspecified site | N |
| 8 | Other upper respiratory disease | N |
| 9 | Unspecified symptom associated with female genital organs | N |
| 10 | Chronic vascular insufficiency of the intestine | N |

| HAE Score: | 0.0000 |
|---|---|
| Action: | HAE Unlikely - No Action Needed |

HAE Score: 0.0000
Action: HAE Unlikely - No Action Needed — 350

300

Procedures 330

| Item # | Description | Present |
|---|---|---|
| 1 | Office or other outpatient visit for the evaluation and management of an established patient | N |
| 2 | Other laboratory | N |
| 3 | Laboratory: chemistry and hematology | N |
| 4 | Other therapeutic procedures | N |
| 5 | Pathology | N |
| 6 | Other diagnostic radiology and related techniques | N |
| 7 | Microscopic examination (bacterial smear, culture, toxicology) | N |
| 8 | Nonoperative urinary system measurements | N |

Procedures 340

| Item # | Description | Present |
|---|---|---|
| 1 | Office or other outpatient visit for the evaluation and management of an established patient | N |
| 2 | Other laboratory | N |
| 3 | Laboratory: chemistry and hematology | N |
| 4 | Other therapeutic procedures | N |
| 5 | Pathology | N |
| 6 | Other diagnostic radiology and related techniques | N |
| 7 | Microscopic examination (bacterial smear, culture, toxicology) | N |
| 8 | Nonoperative urinary system measurements | N |

300

HAE Score: 0.0000
Action: HAE Unlikely - No Action Needed  ⎬ 350

| Drugs | | | 360 |
|---|---|---|---|
| Item # | Description | | Present |
| 1 | Androgens and combinations | | N |
| 2 | Blood derivatives | | N |
| 3 | Unspecified agents | | N |
| 4 | Sympathomimetic agents | | N |
| 5 | Adrenals and combinations | | N |
| 6 | Analgesics/antipyretics; opiate agonists | | N |
| 7 | Antibiotics: penicillins | | N |
| 8 | Antibiotics: erythromycin and macrolide | | N |
| 9 | Analgesics/antipyretics; nonsteroidal anti-inflammatory drugs | | N |

| Drugs | | 370 |
|---|---|---|
| Item # | Description | Present |
| 1 | Androgens and combinations | N |
| 2 | Blood derivatives | N |
| 3 | Unspecified agents | N |
| 4 | Sympathomimetic agents | N |
| 5 | Adrenals and combinations | N |
| 6 | Analgesics/antipyretics; opiate agonists | N |
| 7 | Antibiotics: penicillins | N |
| 8 | Antibiotics: erythromycin and macrolide | N |
| 9 | Analgesics/antipyretics; nonsteroidal anti-inflammatory drugs | N |

HAE Score: 0.0000
Action: HAE Unlikely - No Action Needed  ⎬ 350

| Provider Visits | | 380 |
|---|---|---|
| Item # | Description | Present |
| 1 | Allergy & Immunology | N |
| 2 | Emergency Medicine | N |
| 3 | Acute Care Hospital | N |
| 4 | Home Health Organization/Agency | N |
| 5 | Pharmacy | N |
| 6 | Laboratory | N |
| 7 | Radiology | N |
| 8 | Pulmonary Disease | N |
| 9 | Pediatric Allergy & Immunology | N |

| Provider Visits | | 390 |
|---|---|---|
| Item # | Description | Present |
| 1 | Allergy & Immunology | N |
| 2 | Emergency Medicine | N |
| 3 | Acute Care Hospital | N |
| 4 | Home Health Organization/Agency | N |
| 5 | Pharmacy | N |
| 6 | Laboratory | N |
| 7 | Radiology | N |
| 8 | Pulmonary Disease | N |
| 9 | Pediatric Allergy & Immunology | N |

Within past year, does patient report:

Symptoms/Diagnoses 410

| Item # | Description | Present |
|---|---|---|
| 1 | Diagnosis 1 | N |
| 2 | Diagnosis 2 | N |
| 3 | Diagnosis 3 | N |
| 4 | Diagnosis 4 | N |
| 5 | Diagnosis 5 | N |
| 6 | Diagnosis 6 | N |
| 7 | Diagnosis 7 | N |
| 8 | Diagnosis 8 | N |
| 9 | Diagnosis 9 | N |
| 10 | Diagnosis 10 | N |
| 11 | Diagnosis 11 | N |

Procedures 430

| Item # | Description | Present |
|---|---|---|
| 1 | Procedure 1 | N |
| 2 | Procedure 2 | N |
| 3 | Procedure 3 | N |
| 4 | Procedure 4 | N |
| 5 | Procedure 5 | N |
| 6 | Procedure 6 | N |
| 7 | Procedure 7 | N |
| 8 | Procedure 8 | N |
| 9 | Procedure 9 | N |
| 10 | Procedure 10 | N |
| 11 | Procedure 11 | N |

Disease Score: 0.0000
Action: Disease Unlikely - No Action Needed  — 450

Does patient have prior history of:

Symptoms/Diagnoses 420

| Item # | Description | Present |
|---|---|---|
| 1 | Diagnosis 1 | N |
| 2 | Diagnosis 2 | N |
| 3 | Diagnosis 3 | N |
| 4 | Diagnosis 4 | N |
| 5 | Diagnosis 5 | N |
| 6 | Diagnosis 6 | N |
| 7 | Diagnosis 7 | N |
| 8 | Diagnosis 8 | N |
| 9 | Diagnosis 9 | N |
| 10 | Diagnosis 10 | N |
| 11 | Diagnosis 11 | N |

Procedures 440

| Item # | Description | Present |
|---|---|---|
| 1 | Procedure 1 | N |
| 2 | Procedure 2 | N |
| 3 | Procedure 3 | N |
| 4 | Procedure 4 | N |
| 5 | Procedure 5 | N |
| 6 | Procedure 6 | N |
| 7 | Procedure 7 | N |
| 8 | Procedure 8 | N |
| 9 | Procedure 9 | N |
| 10 | Procedure 10 | N |
| 11 | Procedure 11 | N |

Disease Score: 0.0000
Action: Disease Unlikely - No Action Needed  — 450

Select Disease Score threshold for referral:

Threshold: 0.997
TPR/Sensitivity/Recall: 0.00244
TNR/Specificity: 1.00000
PPV/Precision: 1.00000
FPR: 0.0E+00
AUC: 0.74692
— 460

FIG. 4

IMPLEMENTATION OF MACHINE-LEARNING BASED QUERY CONSTRUCTION AND PATTERN IDENTIFICATION THROUGH VISUALIZATION IN USER INTERFACES

CROSS REFERENCE TO RELATED APPLICATION

This application claims priority to U.S. Provisional Application No. 62/783,155 filed Dec. 20, 2018, entitled, "IMPLEMENTATION OF MACHINE-LEARNING BASED QUERY CONSTRUCTION AND PATTERN IDENTIFICATION THROUGH VISUALIZATION IN USER INTERFACES" which is incorporated herein by reference in its entirety.

BACKGROUND OF INVENTION

Health patterns indicative of certain health conditions are often difficult to identify. This is true for diseases and medical conditions that are readily known to the general population, as well as with diseases that are so rare that they affect only a small portion of the population.

Some diseases, although known to the general public, are clinically diagnosed through exclusion. Thus, a diagnosis of the disease can be delayed as each other possibility is systematically excluded. This prolonged diagnostic time can be detrimental as it delays initiating approved treatments and the progression of the disease for an undiagnosed patient can preclude that patient, when finally diagnosed, from enrolling in a clinical trial and/or a given therapy not having any effect, since the disease can have progressed to a state where the therapy is no longer effective.

A disease is defined as rare (orphan) if it affects fewer than 200,000 people in the US; there are about 7,000 types of such rare disorders. Most of these diseases are genetic, frequently misdiagnosed for years, and without FDA-approved drug treatment. Timely discovery of misdiagnosed and underdiagnosed patients is crucial for their survival and for the proper development and delivery of the right therapeutics (including niche drugs developed by pharmaceutical companies specifically for these rare conditions). The problem of finding potentially undiagnosed subjects for orphan diseases is that active surveillance for such conditions (canvassing a segment of population with questionnaires and/or tests) is expensive and impractical for rare (or even not so rare) diseases, and passive surveillance has to rely on existing medical records (produced by hospitals and insurance companies), which can be incomplete, unreliable, and not contain enough information relevant for the predictive diagnostics. Challenges in identifying these orphan diseases from population-related data exist based on both the limitations of present computing solutions to process the volume of data efficiently and the lack of knowledge regarding what parameters should be searched within this large volume.

The challenges related to establishing patterns that identify an event in a large volume of data and actually identifying that event in this large volume are not unique to disease or to orphan disease identification.

SUMMARY OF INVENTION

Shortcomings of the prior art are also overcome and additional advantages are provided through the provision of a method for determining a probability of the presence of a given medical condition based on a data set related to a patient and providing the probability to a user as a score, the method includes: obtaining, by one or more processors in a distributed computing environment, one or more data sets related to a patient population diagnosed with a medical condition from one or more databases; based on a frequency of features in the one or more data sets, identifying, by the one or more processors, common features in the one or more data sets; generating, by the one or more processors, one or more patterns comprising a portion of the common features; generating, by the one or more processors, one or more machine learning algorithms based on the one or more patterns, the one or more machine learning algorithms to identify presence or absence of the given medical condition in an undiagnosed patient; utilizing, by the one or more processors, statistical sampling to compile a training set of data, wherein the training set comprises data from the one or more data sets and at least one additional data set comprising data related to a population without the medical condition, and wherein utilizing the statistical sampling comprises formulating and obtaining queries based on the data set and processing and responding to the queries; tuning, by the one or more processors, the one or more machine learning algorithms by applying the one or more machine learning algorithms to the training set of data; integrating, by the one or more processors, the one or more machine learning algorithms into a graphical user interface, wherein the graphical user interface provides an input to enable a user to provide data related to the undiagnosed patient; obtaining, by the one or more processors, via the graphical user interface, data related to the undiagnosed patient; applying, by the one or more processors, the one or more machine learning algorithms to the data related to the undiagnosed patient; determining, by the one or more processors, based on applying the one or more machine learning algorithms to the data related to the undiagnosed patient, a probability, wherein the probability is a numerical value indicating a percentage of commonality between the data related to the undiagnosed patient and the one or more patterns; and displaying, by the one or more processors, the probability to the user, through the graphical user interface, as a score.

Shortcomings of the prior art are also overcome and additional advantages are provided through the provision of a system for determining a probability of the presence of a given medical condition based on a data set related to a patient and providing the probability to a user as a score. The system includes: a memory; one or more processors in communication with the memory; program instructions executable by the one or more processors via the memory to perform a method, the method comprising: obtaining, by the one or more processors in a distributed computing environment, one or more data sets related to a patient population diagnosed with a medical condition from one or more databases; based on a frequency of features in the one or more data sets, identifying, by the one or more processors, common features in the one or more data sets; generating, by the one or more processors, one or more patterns comprising a portion of the common features; generating, by the one or more processors, one or more machine learning algorithms based on the one or more patterns, the one or more machine learning algorithms to identify presence or absence of the given medical condition in an undiagnosed patient; utilizing, by the one or more processors, statistical sampling to compile a training set of data, wherein the training set comprises data from the one or more data sets and at least one additional data set comprising data related to a population without the medical condition, and wherein utilizing the statistical sampling comprises formulating and obtaining queries based on the data set and processing and responding to the queries; tuning, by the one or more processors, the one or more machine learning algorithms by applying the one or more machine learning algorithms to the training set of data; integrating, by the one or more processors, the one or more machine learning algorithms into a graphical user interface, wherein the graphical user interface provides an input to enable a user to provide data related to the undiagnosed patient; obtaining, by the one or more processors, via the graphical user interface, data related to the undiagnosed patient; applying, by the one or more processors, the one or more machine learning algorithms to the data related to the undiagnosed patient; determining, by the one or more processors, based on applying the one or more machine learning algorithms to the data related to the undiagnosed patient, a probability, wherein the probability is a numerical value indicating a percentage of commonality between the data related to the undiagnosed patient and the one or more patterns; and displaying, by the one or more processors, the probability to the user, through the graphical user interface, as a score.

Shortcomings of the prior art are also overcome and additional advantages are provided through the provision of a computer program product for determining a probability of the presence of a given medical condition based on a data set related to a patient and providing the probability to a user as a score. The computer program product includes: a computer readable storage medium readable by one or more processors in a distributed computing environment, and storing instructions for execution by the one or more processors for performing a method comprising, the method comprising: obtaining, by the one or more processors in a distributed computing environment, one or more data sets related to a patient population diagnosed with a medical condition from one or more databases; based on a frequency of features in the one or more data sets, identifying, by the one or more processors, common features in the one or more data sets; generating, by the one or more processors, one or more patterns comprising a portion of the common features; generating, by the one or more processors, one or more machine learning algorithms based on the one or more patterns, the one or more machine learning algorithms to identify presence or absence of the given medical condition in an undiagnosed patient; utilizing, by the one or more processors, statistical sampling to compile a training set of data, wherein the training set comprises data from the one or more data sets and at least one additional data set comprising data related to a population without the medical condition, and wherein utilizing the statistical sampling comprises formulating and obtaining queries based on the data set and processing and responding to the queries; tuning, by the one or more processors, the one or more machine learning algorithms by applying the one or more machine learning algorithms to the training set of data; integrating, by the one or more processors, the one or more machine learning algorithms into a graphical user interface, wherein the graphical user interface provides an input to enable a user to provide data related to the undiagnosed patient; obtaining, by the one or more processors, via the graphical user interface, data related to the undiagnosed patient; applying, by the one or more processors, the one or more machine learning algorithms to the data related to the undiagnosed patient; determining, by the one or more processors, based on applying the one or more machine learning algorithms to the data related to the undiagnosed patient, a probability, wherein the probability is a numerical value indicating a percentage of commonality between the data related to the undiagnosed patient and the one or more patterns; and displaying, by the one or more processors, the probability to the user, through the graphical user interface, as a score.

Computer systems, computer program products, and methods relating to one or more aspects of the technique are also described and can be claimed herein. Further, services relating to one or more aspects of the technique are also described and can be claimed herein.

In some embodiments of the present invention, the program code obtaining the one or more data sets includes: the program code converting the one or more data sets into a standardized format, wherein the formatted data is utilized for the identifying.

In some embodiments of the present invention, a portion of the obtained data is machine readable.

In some embodiments of the present invention, the program code identifies the common features by utilizing a method selected from the group consisting of: weighting the common features based on frequency of occurrence in the one or more data sets, wherein the common features comprise mutual information, performing diffusion mapping, performing principal component analysis, performing recursive feature elimination, and utilizing a Random Forest to select the features.

In some embodiments of the present invention, the program code obtains, via the graphical user interface, additional data related to the undiagnosed patient. The program code applies the one or more machine learning algorithms to the additional data related to the undiagnosed patient. The program code automatically updates, based on applying the one or more machine learning algorithms to the additional data related to the undiagnosed patient, the probability. The program code displays the updated probability to the user, through the graphical user interface, as a score.

In some embodiments of the present invention, the program code determines if the probability exceeds a pre-determined threshold and based on determining that the probability exceeds the pre-determined threshold, the program code automatically transmits the probability to at least one administrator of the one or more databases.

In some embodiments of the present invention, the program code obtains, after a pre-determined period of time, via the graphical user interface, current data related to the undiagnosed patient. The program code determines if the current data is consistent with the probability. Based on the determining, the program code adjusts the one or more machine learning algorithms.

In some embodiments of the present invention, the program code determines if the score meets a predetermined threshold. Based on determining that the score meets the threshold, the program code automatically generates an electronic referral. The program code transmits the electronic referral to a healthcare provider.

Additional features are realized through the techniques of the present invention. Other embodiments and aspects of the invention are described in detail herein and are considered a part of the claimed invention.

BRIEF DESCRIPTION OF DRAWINGS

One or more aspects of the present invention are particularly pointed out and distinctly claimed as examples in the claims at the conclusion of the specification. The foregoing and objects, features, and advantages of one or more aspects of the invention are apparent from the following detailed description taken in conjunction with the accompanying drawings.

FIG. 2, which is segmented into FIGS. 2A-2C, depicts a graphical user interface that comprises various aspects of some embodiments of the present invention.

FIG. 3, which is segmented into FIGS. 3A-3B, depicts a graphical user interface that comprises various aspects of some embodiments of the present invention.

FIG. 4 depicts a graphical user interface that comprises various aspects of some embodiments of the present invention.

DETAILED DESCRIPTION OF THE INVENTION

Figure 1:
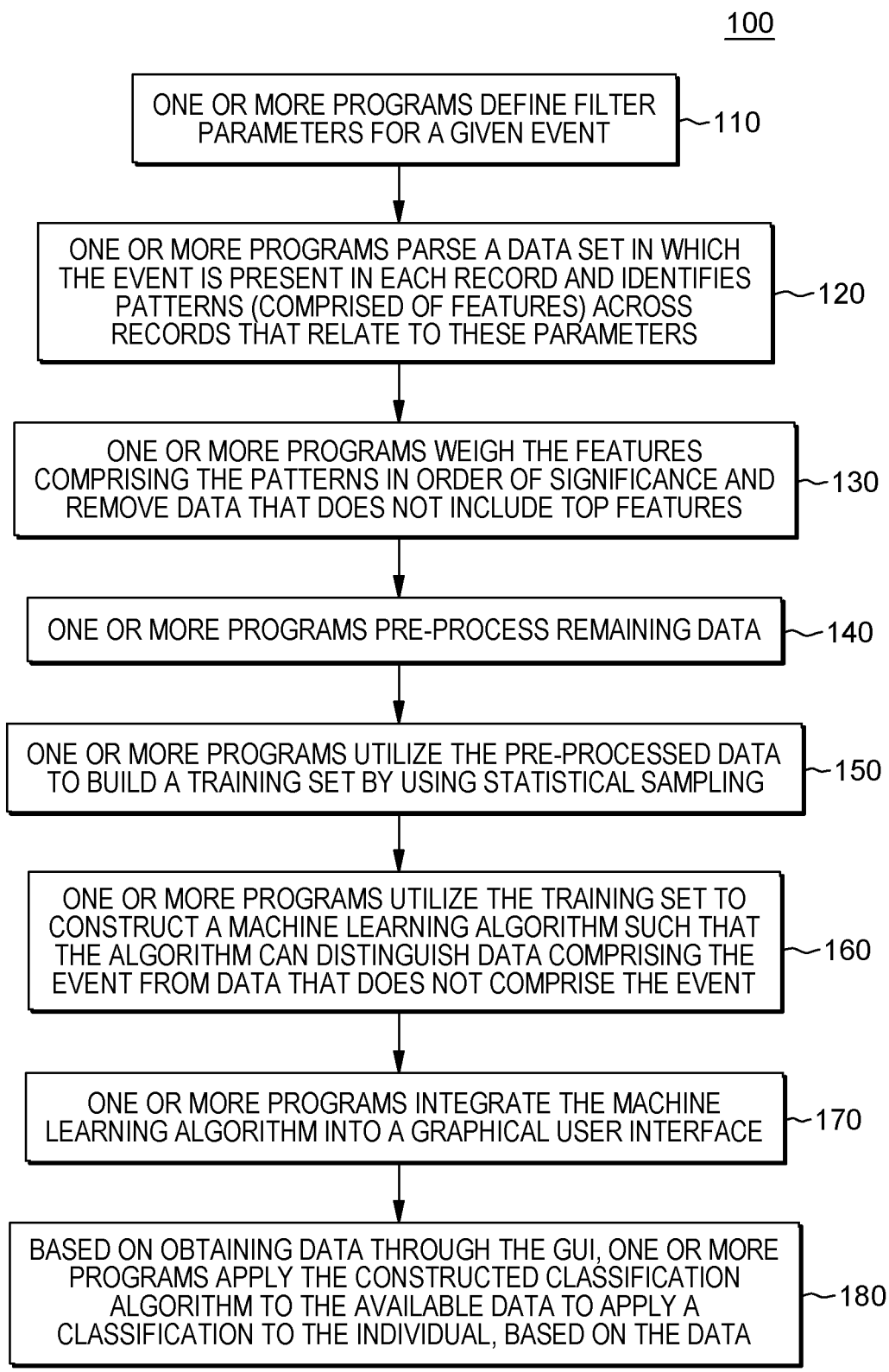
FIG. 1 depicts a workflow associated with aspects of embodiments of the present invention.

Aspects of the present invention and certain features, advantages, and details thereof, are explained more fully below with reference to the non-limiting examples illustrated in the accompanying drawings. Descriptions of well-known materials, fabrication tools, processing techniques, etc., are omitted so as not to unnecessarily obscure the invention in detail. It should be understood, however, that the detailed description and the specific examples, while indicating aspects of the invention, are given by way of illustration only, and not by way of limitation. Various substitutions, modifications, additions, and/or arrangements, within the spirit and/or scope of the underlying inventive concepts will be apparent to those skilled in the art from this disclosure. The terms software, program code, and one or more programs are used interchangeably throughout this application.

The term "diagnose" is utilized throughout the application to suggest that a data model that is generated and method determining a probability of the presence of a given physical or medical condition, including but not limited to a disease or an orphan disease, based on a data set related to an individual, referred to herein as a patient. However, the so-called diagnosis provided by aspects of embodiments of the present invention is not analogous to a medical diagnosis, provided by a health professional, often based on the result of a medical text or procedure. Rather, a diagnosis herein can be understood as a recognition of a pattern, or a given portion of a pattern, where the pattern was generated as described herein, in embodiments of the present invention.

Embodiments of the present invention combine data analytics and pattern prediction to enable program code executing on at least one processor to identify patterns within a data set in the absence of advance data defining the pattern. In an embodiment of the present invention, program code analyzes a data set to identify parameters comprising data points characteristic of a certain condition (e.g., a physical condition). The program code adapts a machine learning algorithm to utilize these parameters to identify data consistent with this condition and utilizing data sets of sizes which cannot be analyzed by a human or by a computing environment that does not adequately distribute processing tasks related to the analysis. The program code identifies these parameters in the absence of established data characterizing the condition. This approach can be utilized to determine recognition patterns to identify diseases, including orphan diseases, in a data set that includes data related to individuals with this condition and subsequently, to identify these patterns in an unlimited data set where the prevalence of individuals with this condition is unknown. However, this approach is not merely limited to physical condition (e.g., disease) identification, but can be utilized in general to predict criteria identifying an event and apply these criteria across a data set that is not constrained by size or complexity. Additionally, in embodiments of the present invention, the predictions are provided to users through a graphical user interface (GUI) in a manner that enables users to easily view and access the generated data model underlying the predictions, as well as manipulate the underlying data to enhance the accuracy of the predictions. The data is visualized in a time-sensitive manner and the GUI generated by program code in embodiments of the present invention provides initial as well as enhanced results to a user, in real-time and near real-time, as the user utilizes the GUI. Throughout this specification, aspects of embodiments of the present invention are applied to the task of physical (or medical) condition (e.g., disease) identification. However, this singular (non-limiting) application of aspects of embodiments of the present invention is offered to illustrate the functionality of the present invention, as understood by one of skill in the art.

As will be discussed herein, various issues exist when attempting to identify a probability of a medical condition in an individual, especially if the condition is rare because a profile for certain diagnosis does not exist. To address this issue, embodiments of the present invention comprise a computing network-based patient management method that collects, converts (if needed), and consolidates patient information from various sources, including but not limited to, physicians and health-care providers, into a standardized format, stores it in network-based storage devices, utilizes it to create models for identification of the conditions, and provides it to clinicians in a GUI in a dynamic visualization that enables clinicians to provide risk data to patients in a timely manner, based both on the data that is stored and data received from the patient, in real-time. The method provides a graphical user interface (GUI) that can be generated by a content server, which is hardware or a combination of both hardware and software. A user, such as a health care provider or patient, is given remote access through the GUI to view or update information about a patient's medical condition using the user's own local device (e.g., a personal computer or wireless handheld device). Based on the data received, the program code regenerates the risks (scores), to reflect a more current risk for one or more conditions. When a user wants to update the records, the user can input the update in any format used by the user's local device. In some embodiments of the present invention, whenever the patient information is updated, the program code converts the data to a standardized format and stores the data in the collection of medical records, on one or more of the network-based storage devices. In some embodiments of the present invention, after the updated information about the patient's condition has been stored in the collection, the content server, which is connected to the network-based storage devices, immediately updates the risk score based on the updated information about the patient's condition. This updated risk can be transmitted, by the program code, in a standardized format over the computer network to all physicians and health-care providers that have access to the patient's information (e.g., to a medical specialist to review the updated information about the patient's medical condition), so that all users can quickly be notified of any changes without having to manually look up or consolidate all of the providers' updates. This ensures that any user of the GUI can have access to the data model and its functionality such that an immediate result can be obtained, based on all the available data, regardless of the location of use and the type of user.

Embodiments of the present invention provide a benefit over existing systems based on the ability to provide a clear value that represents a risk, and adjust that value, in real-time, based on existing and new data, from a variety of sources. Thus, the data, from a wide variety of sources, many of which are only machine-readable, are made available in a manner that is user-friendly, consistent, and dynamic. In some embodiments of the present invention, the program code obtains the data and converts the data such that it can be utilized by the program code in a standardized format. In order to standardize certain of the data, various application programming interfaces (APIs) can be utilized by the program code, including natural language processing APIs. In some embodiments of the present invention, the data is converted to a standardized format by one or more processors executing on a server that can be understood as a content server, as this content server also executed program code that generates the GUI, to provide access to the results generated from the data.

Advantages provided by aspects of some embodiments of the present invention include: (1) the ability to identify features that differentiate individuals with certain medical conditions from the general population, prior to these individuals receiving a formal diagnosis of the medical condition, (2) the ability to determine potential predictors of a future formal diagnosis of a medical condition, (3) the ability to demonstrate the appearance of symptoms of the medical condition earlier than currently understood by the medical community, (4) the ability to provide the potential to accelerate clinical diagnosis of the medical condition, and (5) the ability to provide complex data related to potential predictors of a future formal diagnosis of a medical condition in a transparent and user-friendly manner to health support personnel, including but not limited to, clinicians.

Certain embodiments of the present invention represent improvements over known methods of data identification, both in the application of identifying individuals with physical/medical conditions, as well as in data management and data mining in general. For example, embodiments of the present invention enable the determination and identification of patterns based on an unlimited number of factors, given the ability of the program code to mine large data stores. For example, when applied to creating a profile (e.g., a disease or medical condition profile) and identifying individuals that fit this profile, relevant features that the program code builds into a pattern for later identification of individuals that fit this pattern are not solely based on diseases, but on drugs and procedures as well, which expands the information content that can be leveraged by the overall process. Embodiments of the present invention increase computational efficiency because, when building a profile to identify a given quality, the program code selects relevant features using not just prior knowledge and frequency count, but ultimate information theory mechanisms, including mutual information, and weight the variety of information utilized by, for example, truncating a the set of obtained features to establish a level of significance for each identified feature using the mutual information metric.

Mutual information is an example of a method that can be utilized to identify features in an embodiment of the present invention. Further embodiments of the present invention utilize varying techniques to select features, including but not limited to, diffusion mapping, principal component analysis, recursive feature elimination (a brute force approach to selecting features), and/or a Random Forest to select the features. Embodiments of the present invention that utilize mutual information, diffusion mapping, and a Random Forest can provide certain efficiency advantages.

Aspects of embodiments of the present invention represent improvements to existing computing technology and are inextricably tied to computing. Specifically, embodiments of the present invention represent improved methods of handling large volumes of data and for building machine learning models from the data. For example, embodiments of the present invention reduce the observed data rate in the eventual results because the program code preprocesses the data utilized to build a pattern, rather than using a less efficient binary binning procedure. Embodiments of the present invention are also inextricably linked to computing because program code in embodiments of the present invention utilizes unique features of user interfaces of both proprietary and third party software in order to provide users with an effective visualization of complex data. Additionally, GUIs generated by the program code in embodiments of the present invention provide users, such as clinicians, with an ability to interact with the machine learning models generated by embodiments of the present invention, increasing the intelligence and functionality of these models, through use.

Aspects of embodiments of the present invention are inextricably tied to computing at least because the electronic models, including disease or medical condition models, generated by embodiments of the present invention cannot be generated outside of computing and do not exist outside of computing. Records initially utilized in embodiments of the present invention are electronic records in one or more data set, contained in one or more database, that are machine readable. The resultant models are also electronic and are applied to additional electronic data sets utilizing computing resources. Because of both the volume and the nature of data, an individual is not capable of accomplishing the specific aspects of embodiments of the present invention that result in a machine readable data model that can be applied by program code to additional data sets in order to identify records with a probability of an event or condition that the model was generated to predict the probable presence of. Additionally, the methods of presenting certain of the results to users in embodiments of the present invention, and enabling users to interact with and manipulate the results, to further train the machine learning algorithm, are inextricably tied to the functionality of GUIs provided in computing resources and the ability of the program code to take advantage of the features inherent in GUIs.

Embodiments of the present invention integrate functionality into a practical application at least because embodiments of the present invention can produce outputs that are immediately usable by users, including but not limited to medical personnel, in a manner that individuals and existing systems are incapable of because of the speed at which the embodiments of the present invention are able to provide results. To be useful, and hence provide a practical application, program code in embodiments of the present invention both generates and updates models and provides results (identification of records that comport with the model), within a limited temporal period. For example, in a scenario where an individual visits a healthcare provider, the individual and the provider would benefit from acquiring information regarding whether the individual, as represented by an electronic medical record, has items in the record that match the data sought by one or more disease models. If this information cannot be provided within the visit, it is arguably not useful to the individual or the healthcare provider. Thus, in embodiments of the present invention, the program code analyzes an individual record and applies disease models in real-time, or close to real-time. Thus, embodiments of the present invention enable real-time analysis of an electronic medical records of a given individual based on whether the individual's medical records includes one or more patterns determined by program code in embodiments of the present invention. Timing advantages provided by embodiments of the present invention are particularly useful because the timing of a diagnosis can be determinative regarding whether the condition can be treated (and as explained herein, data provided by the program code in embodiments of the present invention can aid a medical professional in making a diagnosis). For example, individuals are only admitted to clinical trials when a given condition has not progressed beyond a certain point. Thus, the ability of the program code to timely present users with data patterns that are consistent with a particular medical issue in real-time or close to real-time is, for example, a practical application of the unique data analytics utilized herein. Additionally, therapies and treatments for a given condition cannot be effective because the disease has progressed to a state where the therapies or treatments are no longer effective. Timing advantages are realized prominently through the user of a particular GUI referred to as a Scorecard GUI. The Scorecard GUI, which will be discussed in greater detail herein, enables real-time manipulation of classifications and thus, utilization of the classification algorithms. The program code simplifies complex classification results into a "score" while providing transparency to human-comprehensible factors that contributed to the score. Thus, program code both provides and manipulates the score, in the GUI, in real-time, based upon entries made into the GUI. The timing of this accessibility to data as well as the accessibility to the data itself both represent practical applications of aspects of embodiments of the present invention.

In certain embodiments of the present invention, the program code predicts and detects patterns in data by utilizing Support Vector Machines (SVMs). In an aspect of an embodiment of the present invention, the program code trains a linear SVM classification algorithm for segregating database entries, for example, to separate entries representing individuals with a given condition from entries representing individuals that do not have the condition. In an embodiment of the present invention, the program code utilizes linear SVM, rather than, for example, logistic regression, Random Forest (RF) grouping algorithms, and/or other simple statistical approaches, to achieve a best available classification performance. Another advantage of certain embodiments of the present invention that utilize SVM is that the program code can apply the SVM score of the false positive data as a mechanism to sort out the most promising subjects. (Certain embodiments of the present invention do utilize RF grouping algorithms and logistic regression with SVM in order to achieve hyper-parameter optimization.)

Embodiments of the present invention provide advantages and improvements that are inextricably tied to computer technology also because embodiments of the present invention offer certain advantages that increase computational efficiency and efficacy. For example, as described in greater detail later on, embodiments of the present invention utilize distributed processing based on anticipated query results in order to decrease the timeline for key analytic deliverables. This distributed processing enables the program code to perform multiple analysis processes simultaneously. Portions of certain embodiments of the present invention can be migrated to a cloud architecture and made available to users as software as a service (SaaS) offerings. The unlimited computational capacity of resources in a cloud architecture are suited to support the program code's distribution of simultaneous queries and processes in order to meet the efficiency demands of the system in a data rich environment.

Embodiments of the present invention also provide advantages and improvements that are inextricably tied to computer technology because they utilize machine learning. One advantageous aspect of some embodiments of the present invention over existing approaches to event (e.g., condition) identification in data dense environments is that some other methods approach the problem of event identification and recognition as a statistical problem, instead of a machine learning one, which is an approach that limits the options in available tools. By utilizing machine learning, embodiments of the present invention can identify records that include an event where the information directly identifying the event is absent. For example, by using machine learning, program code can identify patients with a given disease in a data set of undiagnosed patients, i.e., where the data does not already indicate that the disease is present in the patient. In some cases, the program code can utilize machine learning to assist indicating to a user, output suggesting that an individual is infected with a disease when the opposite is indicated in data related to that individual. Thus, the program code is not merely identifying and retrieving existing established data stored in one or more memory device. Rather, the program code establishes a pattern, continuously trains a machine learning algorithm to apply the pattern, and utilizes the algorithm to identify instances of an event not already explicitly indicated by the data utilizing this pattern. As described in greater detail herein, the machine learning algorithm to apply the pattern applied the patterns in a user-friendly interface which can be understood as a Scorecard. This Scorecard provides a utility to users, who can then access and interact with complex data in a practical manner.

Embodiments of the present invention provide advantages over known diagnostic systems when utilized to determine mutual information and apply this information to an analysis of a data set where the presence of the event related to the mutual information is unknown, at least because the process is devoid of selection bias. Returning to the disease example, in some embodiments of the present invention, there are no assumptions regarding an individual that are carried into the program code and the program code performs its analyses consistently. Selection bias is an issue when attempting to identify a medical condition as a medical professional can be prone to certain conclusions based on, for example, past experience. Expanding on the disease example, this issue can be problematic both with orphan diseases as well as for diseases for which doctors make a medical diagnosis as a result of eliminating other possibilities. For example, in the area of orphan disease identification, this bias is especially problematic because the rarity of an orphan disease means that a medical professional can come into contact with very few people, or even no people at all, with a given condition, until a certain patient presents the condition.

Embodiments of the present invention also provide advantages over existing approaches because of the applicability of the classification algorithms utilized (to classify individuals as exhibiting patterns related to diseases that should be worthy of further attention, including but not limited to, classifying individuals in Amyotrophic Lateral Sclerosis (ALS)/non-ALS classifications and/or individuals with Hereditary Angioedema (HAE)/non-HAE classifications) to clinical decision support. For example, the patterns generated by the program code in embodiments of the present invention can be integrated into clinical decision support tools (and as explained with the Scorecard, the program code itself can generate a decision support tool/GUI) to aid in the evaluation of patient suspected by a clinician of having a given condition, including but not limited to, ALS or HAE (or more broadly, the disease classification algorithm to aid in clinical evaluation of a patient suspected of having the disease). For illustrative purposes only, some specific examples, such as FIG. 2, are provided that are configured for uses related to ALS and FIG. 3, is provided and is configured for use with HAE. These specific examples are utilized to provide illustrative examples that are easy to comprehend and not to suggest any limitation. A generic example of visualization is provided in FIG. 4, but FIGS. 2-3 were included in order to demonstrate particular applications. As demonstrated in FIGS. 2-4, which are discussed in greater detail herein, results of the data processing in embodiments of the present invention can be integrated into graphical user interfaces (GUIs), which are user-friendly and can be utilized by clinicians when evaluating a given patient. For example, during a meeting (appointment) a patient can offer information and the features comprising patient-reported information collected by a clinician through a patient interview (as well as through integration with medical records systems and other medical data) regarding the patient's medical history. The program code, as integrated into the GUI, can map the features to the features learned by the algorithm through analyses of patient histories contained in claims, EHR, etc. The GUI enables a user, such as a clinician, to input disease features observed in a patient. Based on obtaining the disease features via the GUI, the program code outputs a likelihood of disease, based in the input features. In some embodiments of the present invention, the likelihood output by the GUI is based upon the probability calculated by the machine learning algorithm. Thus, embodiments of the present invention include enhancements to user interfaces as well as interfaces that provide an original manner in which to view complex data and outputs of embodiments of the present invention.

As aforementioned, challenges in identifying conditions, including diseases, such as orphan diseases and ALS and HAE, from population-related data exist based on both the limitations of present computing solutions to process the volume of data efficiently and the lack of knowledge regarding what parameters should be searched within this large volume. In the case of orphan diseases, the small number of confirmed cases renders pattern building and recognition challenging, and the case of a disease where a medical diagnosis is the result of eliminating other possibilities renders the same data problems. Regarding the volume of data, embodiments of the present invention can process a large number of patients coded with a large number of universe codes. For example, an embodiment of the present invention can be utilized to process the patient histories of more than 180 million patients, whose records can include more than 10 years of recorded healthcare history. Given the distributed nature of the processing architecture, the number of patients that can be processed/scored is only limited by storage, as the efficiency of the process enables the processing of increasingly large volumes of data.

Workflows of certain embodiments of the present invention can include four stages: data integration, pattern extraction, population separation, and data visualization. FIG. 1 is a workflow 100 that illustrates aspects of embodiments of the present invention, including one or more programs that perform data integration (e.g., patient definition), pattern extraction (e.g., feature extraction), and generate population separation maps (e.g., prediction). Before discussing FIG. 1, FIG. 5 is also a workflow 500 that illustrates these aspects, but in a more general manner for ease of comprehension.

Figure 5:
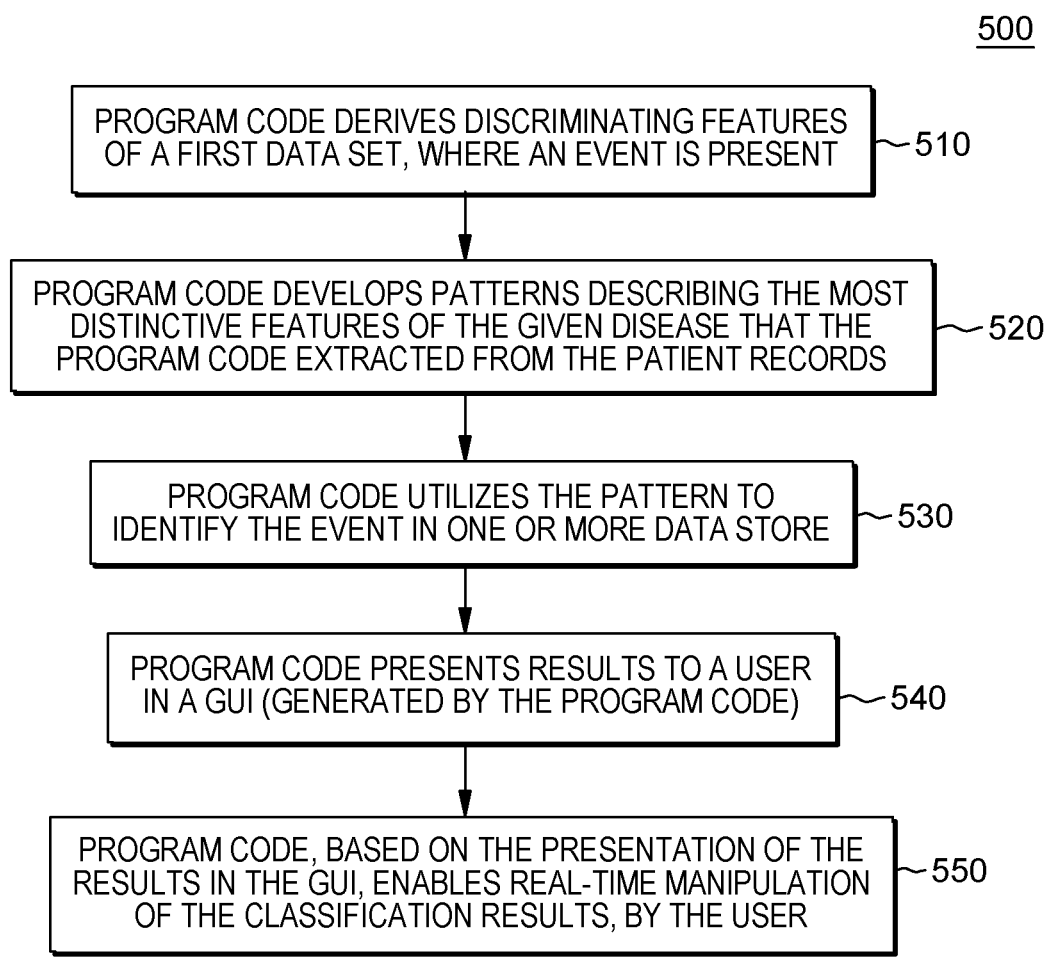
FIG. 5 depicts a workflow associated with aspects of embodiments of the present invention.

Referring to FIG. 5, data integration refers to aspects of embodiments of the present invention in which the program code derives discriminating features of a first data set, where an event is present (510). For example, if the event is a certain disease, the program code can analyze records of individuals medically diagnosed with the disease and extract discriminating features that describe the treatment journey of these patients.

Pattern integration refers to aspects of embodiments of the present invention in which the program code develops a pattern for identifying records with a given event based on using the most distinctive features extracted during data integration. For example, the program code develops patterns describing the most distinctive features of the given disease that the program code extracted from the patient records (520).

Population separation refers to aspects of embodiments of the present invention where the program code utilizes the pattern to identify the event in one or more data store (530). For example, returning to the disease example, by analyzing data resources including records identifying large populations, the program code identifies within the resources which patient clusters match the treatment pathways exhibited by the known sufferers.

Data visualization refers to the program code presenting classification results. In embodiments of the present invention, the program code presents results to a user in a GUI (generated by the program code) (540), and the program code, based on the presentation of the results in a GUI, enables real-time manipulation of the classification results, by the user (550).

Pattern integration, population separation, and data visualization are discussed in U.S. patent application Ser. No. 15/723,861, which is incorporated herein in its entirety for all purposes. The present disclosure focusses on the data visualization aspect of embodiments of the present invention.

In utilizing aspects of embodiments of the present invention to build a data model related to a specific disease and applying that dynamic model to identify individuals that fit the model within a given probability, embodiments of the present invention enable identification of early predictors of the disease by using big data analytics of a large claims database. As aforementioned, FIG. 1 is a workflow 100 that illustrates aspects of embodiments of the present invention, including one or more programs that perform data integration (e.g., patient definition), pattern extraction (e.g., feature extraction), and generate population separation maps (e.g., prediction).

As will be illustrated and discussed herein, one or more programs, executed by at least one processing resource, mine data utilizing various aspects of embodiments of the present invention to identify features in the electronic medical data of patients who were previously medically diagnosed with a given disease. In some embodiments of the present invention, one or more programs in some embodiments of the present invention specifically mine the electronic claim histories of the patients to find factors that differentiate these patients from the general population, even before the patients received the initial diagnosis by a medical professional.

As will be described in more detail below, and as illustrated utilizing FIGS. 1-4, in embodiments of the present invention, one or more programs obtain (in some examples, exclusively) electronic medical records of individuals who were previously medically diagnosed with a disease. The electronic medical records can originate from varying systems and can be human and/or machine readable. In some embodiments of the present invention, the program code converts the electronic medical records to a single format. To make this conversion, the program code can employ one or more existing API, including but not limited to a natural language processing (NLP) API. The one or more programs analyze (mine) the data utilizing both frequency ranking and by identifying mutual information. Thus, the program code in some embodiments of the present invention employs an analysis that utilizes two data-ranking methods: a frequency method and a mutual information method. The program code utilizes the mutual information measure to quantify the statistical relevance of every feature in the electronic data set(s) of medical records to a future diagnosis of a given disease. The program code computes the relative frequency of pertinent events to rank the differentiating features based on the mutual information measure. Based on frequency ranking and mutual information, the one or more programs identify distinguishing features in categories that include diagnoses, procedures, drugs, providers, and locations. Based on identifying the distinguishing features, the one or more programs generate predictors (e.g., an adaptive data model), that the one or more programs can apply to data sets where it is unknown whether the individuals represented have the given disease, and based on applying the model, the one or more programs can identify probabilities of the given disease being present among the individuals represented.

Returning to FIG. 1, FIG. 1 is an example of a workflow 100 of an embodiment of the present invention which includes, as described above, data integration, pattern extraction, population separation, and data visualization. Referring to FIG. 1, in some embodiments of the present invention, the program code defines filter parameters for a given event (110). The filter parameters include data points where patterns could be relevant to the event. For example, if the event is the diagnosis of a given disease, filter parameters can include one or more of disease/diagnostic codes for various comorbid conditions, prescription drugs, inpatient and/or outpatient procedures to diagnose and/or treat symptoms of the disease, visits to specialists, etc. In an embodiment of the present invention, the disease/diagnostic codes can comprise diagnostic codes, such as International Statistical Classification of Diseases and Related Health Problems codes, referred to as ICD-9 codes and the newer ICD-10 codes.

Based on the filter parameters, the program code parses a data set in which the event is present in each record and identifies patterns (comprised of features) across records that relate to these parameters (120). For a given disease (as the event), the program code can identify mutual information of all categories of potentially relevant features such as, for example, for comorbid diagnoses, prescription drugs, provider visits, treatment locations, and/or medical procedures.

In an embodiment of the present invention, the data set analyzed by the program code comprises medical information (e.g., records) related to a population of individuals with a given disease. For example, the data set can include, coupled with the timing for each feature, diagnostic codes, $D_x(t)$, (e.g., ICD-9 codes, ICD-10 codes), procedures (e.g., Proc(t)), drug treatments, including prescriptions (e.g., Drug (t)), provider visits (Provider(t), and/or the location(s) of each individual represented in the data set (e.g., Location(t)). Locations can include, but are not limited to, locations of providers who interacted with a patient, a ZIP code related to a practice and/or a patient, a metropolitan area identifier, etc. In some embodiments of the present invention, because data sources mined by the program code are HIPAA compliant, the program code utilizes the first three numbers of the ZIP code of a patient as a patient location. The constant in the data set is that it is a known that each individual represented by the data has a specific medical condition, including a particular disease. The individual factors or features in the data set can also be referred to collectively as codes. One or more programs in an embodiment of a present invention can initially identify a population with a given disease by electronically isolating a group of records that include individuals definitively diagnosed with the disease, by utilizing one or more of an ICD-9 code and/or a ICD-10 code specific to that disease, from all patients in the national dataset that includes the electronic medical records of over ~180 million patients. In order to further isolate a data set for use in predictive feature analyses, the one or more programs filters this initial data (110) by identifying, from these electronic records, records that represented individuals across all the states in the United States with a minimum of one year of adjudicated claims history prior to the implementation of the diagnosis code for the particular disease in the records.

Referring to FIG. 1 and the example of identifying a pattern for a given disease, including an orphan disease, in order to identify patterns (e.g., FIG. 1, 120), in an embodiment of the present invention, program code identifies a patient temporal signal, i.e., the codes and the combination of codes that separate individuals with a given condition, for example, from a general population and/or a specific disease population. In an embodiment of the present invention, the program code utilizes feature selection techniques to identify the mutual information in the data set that can be utilized to characterize the given condition. The program code can utilize this mutual information as an inclusion/exclusion index. For example the codes selected through mutual information provide the inclusion criteria for patients to be selected by one or more programs and conversely, those patients who do not possess any of the codes within this set, are excluded by the one or more programs. The goal of feature selection is to define the smallest subset of features that collectively contain most of the mutually shared information and thus most clearly define the characteristics of a patient with a given disease. The one or more programs determined the relative frequency of pertinent events to rank the differentiate features based on the mutual information measure.

By determining mutual information, the program code in embodiments of the present invention uncovers consistent data over voluminous records that would be impossible outside of the specialized processing, which is discussed herein. In embodiments of the present invention, the program code applies frequency ranking and mutual information procedures to identify the distinguishing features that include diagnoses, procedures, drugs, providers, and locations, which the program code later uses to determine predictors of the condition. The program code can also take into account feature continuity when determining predictors, as different patterns can emerge within the data at different times. For example, for a given disease, the program code can determine that the occurrence of certain patient features increase over time (e.g., in a 5-year cohort), while certain disorders (e.g., nervous system disorders and other connective tissue disease) increase disproportionately as patients approach diagnosis (by a medical professional), and that other medical conditions (e.g., unspecified diseases of the spinal cord and primary lateral sclerosis) change relatively little over time.

Using the described analytic methods, the program code identifies features in the claims histories of individuals who were medically diagnosed with a given disease, that differentiate these individuals from the general population and/or a specific disease population, before they received the disease diagnosis. For example, the program code determines a group of features or a pattern that is common to these individuals at a time when not enough information was available to the medical professional treating the individuals to make the eventual diagnoses. The program code can determine, for a given disease, that medically significant predictors seen in patients who were eventually diagnosed with the disease include, but are not limited to, nervous system disorders, hereditary and degenerative nervous system conditions, connective tissue disease, skin disorders, lower respiratory disease, gastrointestinal disorders, neurologist visits, orthopedic surgeon visits, gastroenterologist visits, non-traumatic joint disorders, otolaryngologist visits, and the use of certain medications, prior to diagnosis. As is discussed herein, upon identifying the differentiated features, the program code analyzes combinatorial features that differentiate undiagnosed patients from the general population and/or a specific disease population, to further characterize early predictors of the disease, and optimize the algorithm differentiating patients with the disease, prior to diagnosis.

Returning to the analysis to generate the predictive model, in embodiments of the present invention, as discussed above, for each category represented in the data set, the program code analyzes items in those categories over time and notes the absence or presence of each item that appears in the data set for each category. Returning to the disease example, in an embodiment of the present invention, the program code separately analyses codes in each of the following categories: $D_x(t)$, Proc(t), Drug(t), Provider(t), Location(t)). The one or more programs considers features including diagnosis codes, procedure codes, medications, standard provider types, and/or standard care facility types.

Table 1 below illustrates an analysis of the program code of the presence and absence of certain items in a given category utilizing the orphan disease identification example. In Table 1, the variables 1 and 0 serve as binary variables and the headings are categorical variable which together represent whether the given item (category) is absent or present at a given time. In the example of Table 1, the diagnosis codes assigned to individuals by medical professionals, in the data set, over time, are analyzed by the program code. In an embodiment of the present invention, the program code repeats this analysis for procedures, drugs, and the locations of the individuals represented in the records in the data set. As is understood by one of skill in the art, program code performing the analysis can identify nuances in the vast data set within a workable timeframe (e.g., during the visit of an individual to a health care provider) based on the utilization of the processing power of the computer system upon which aspects of the present invention are implemented.

TABLE 1

| Pat(N) | $t_1$ | $t_2$ | $t_3$ | ... | $t_n$ |
|---|---|---|---|---|---|
| $D_x1$ | 1 | 0 | 1 | | 1 |
| $D_x2$ | 0 | 1 | 0 | | 0 |
| ... | | | | | |
| $D_xn$ | 1 | 1 | 1 | | 1 |

Referring back to FIG. 1, once the program code has identified patterns, in an embodiment of the present invention, the program code can weigh the features comprising the patterns in order of significance and remove data that do not include top features (130). Embodiments of the present invention employ more than one method of weighing and selecting significant features. The program code can rank the features based on the raw mutual information values. However, in some embodiments of the present invention, the program code can view the output of a classifier, e.g., SVM or random forest that will provide a numerical measure of the feature importance that can then be ranked. In an embodiment of the present invention, the program code can weigh a feature with more mutual information across records as more significant. Thus, the program code selects top features (i.e., features with largest values of mutual information, down to the level of significance) from each of the categories and orders them in descending order (according to the values of mutual information). By removing data that does not include top features, the program code focuses the analysis and increases the efficiency in later identifications. The universe of data related to, for example, individuals suffering from an orphan disease, can be extremely vast, and by weighing features of the data, the program code is able to consolidate the data set into a more manageable amount for processing. In an embodiment of the present invention, the program code determines the frequency of a code and represents this frequency with a number between 0 and 1. The program code utilizes these frequency codes to perform binning based on how often each item occurs within the data set.

For ease of understanding, Table 1 displays binary values (1 and 0), however, a data set that is analyzed can include more than one event in a specific time slot, thus, a binary representation, such as Table 1 is not fully representative of this aspect of an embodiment of the present invention and is offered merely for ease of understanding. In fact, for a specific condition or disease, the table would not be binary, but would contain numerical values as the numerical values would represent frequency of a code appearing in a patients' health journey. In an embodiment of the present invention, the values in a matrix can represent the presence or absence of a code in a patient's history (as seen in Table 1), but can also represent the frequency with which the code occurs in that time slot. For example, if each column represents a month, then the numerical value can represent (1) the absence or presence of a code, (2) the number of times that code appears in that time slot, (3) the average frequency with which that code appears in that time slot, and (4) any function that can be applied to the value to represent events in that time slot.

Returning to FIG. 1, in an embodiment of the present invention, the program code can pre-process remaining data (140). For example, in an embodiment of the present invention, the program code can use a binning procedure using the average value of the corresponding feature as threshold, for example, values above the threshold are coded as 1, and values below it as 0. In an embodiment of the present invention, after pre-processing the remaining data, in embodiments where this part of the process is included, the program code utilizes the pre-processed data or access available data sets to build a training set by using statistical sampling (150). The training set includes data representing the event and data that represent an absence of the event. In some embodiments of the present invention, the training set comprises electronic records that are only readable by a computing resource.

The program code formulates the training set by proportionally selecting representative electronic records from the target and control populations: the target population is the population with the condition (e.g., event, disease) and the control population is the population is the negative case (to distinguish from the target). Thus, in the example where an event is a disease, the training set includes disease entries and healthy entries. The training set, which can be also understood as a control population, in some embodiments of the present invention can be healthy or a differentiating diagnosis disease; the control population can be those patients having a disease that the program code seeks to differentiate from the population with the disease of interest. Departing from the specific disease example, in an embodiment of the present invention, the program code utilizes a test set of training data to train the machine learning algorithm. The training set is selected to include both records with the occurrence or condition the algorithm was generated to identify, and records absent this occurrence or condition. The program code tests/trains the individual features that comprise the mutual information (and/or other technologies discussed herein) selected to identify a given condition, and utilizing voting and ensemble learning, trains the algorithm.

In an embodiment of the present invention, the program code can utilize the training set with the significant patterns identified in the analysis to construct and tune a machine learning algorithm, such that the algorithm can distinguish data comprising the event from data that does not comprise the event (160). The machine learning algorithm can be a linear SVM classification algorithm, which can be utilized with one or more of an RF grouping algorithm and/or a log regression. If the event is a disease, including an orphan disease, the program code can train the machine learning algorithm to separate database entries representing individuals with a disease from entries representing healthy individuals and/or individuals without this particular disease. The program code can utilize the machine learning algorithm, can assign probabilities to various records in the data set during training runs. The program code can continue training the algorithm until the probabilities accurately reflect the presence and/or absence of a condition in the records within a pre-defined accuracy threshold. With certain diseases, the program code utilizes a support vector machine (SVM) classifier. The program code made a selection based on a comparative assessment of various classifiers. When building a model for certain diseases, in some embodiments of the present invention, the program code utilizes Random Forest to generate predictors.

In some embodiments of the present invention, using the disease example, the training set represents a patient population that had the disease. This defined patient population can consist of a constellation of codes, (diagnosis, procedures, drugs, etc.). The machine learning algorithm, which is discussed herein, learns from this defined patient population. In essence, the machine learning algorithm uses a surrogate patient population to find the undiagnosed patients. Stated in another way, the surrogate patient population consists of the patients known to have the disease, and the machine learning algorithms encode their pre-diagnosis characteristics to find similar patients and process the retrospective patient journey to predict the prospective patient journey. In the patient definition process the program code identifies cohort of patients that the machine learning algorithm will learn from; this patient cohort will serve as the training set. In embodiments of the present invention, the internal algorithms applied by the program code include, but are not limited to: 1) mutual information to inform or refine the patient definition; and/or 2) various datamining techniques, including but not limited to, histograms to capture procedures, drugs, diagnosis codes, specialty types, geographic location, patient demographics (age, gender), and co-morbidities.

As aforementioned, in an embodiment of the present invention, the program code constructs the machine learning algorithm, which can be understood as a classifier, as it classifies records (which can represent individuals) into a group with a given condition and a group without the given condition. In an embodiment of the present invention, the program code utilizes the frequency of occurrences of features in the mutual information to identify and filter out false positives. The program code utilizes the classifier to create a boundary between individuals with a condition and the general population (and/or a specific disease population) to lower multi-dimensional planes, given multiple dimensions, including, for example, fifty (50) to one hundred (100) dimensions. When embodiments of the present invention are employed to build a model to predict some diseases, the one or more program employ an ensemble of classifiers developed employing machine learning techniques to optimize the selection and ranking of diagnosis predictors for these diseases.

As part of constructing a classifier (machine learning algorithm), the program code can test the classifier to tune its accuracy. In an embodiment of the present invention, the program code feeds the previously identified feature set into a classifier and utilizes the classifier to classify records of individuals based on the presence or absence of a given condition, which is known before the tuning. As aforementioned, the presence or absence of the condition is not noted explicitly in the records of the data set. When classifying an individual with a given condition utilizing the classifier, the program code can indicate a probability of a given condition with a rating on a scale, for example, between 0 and 1, where 1 would indicate a definitive presence. The classifier can also exclude certain individuals, based on the medical data of the individual, from the condition.

In an embodiment of the present invention, the program code constructs more than one machine learning algorithm, each with different parameters for classification, based on different analysis of the mutual information, and generates an ultimate machine learning algorithm based on an ensemble of these classifiers.

In an embodiment of the present invention, to decrease the instances of false positive results, in an embodiment of the present invention, when the algorithm is an SVM algorithm, the program code collects false positive results and sorts them according to their SVM score in order to identify false positives. In an embodiment of the present invention, to increase the comprehensibility and usability of the result, the program code post-processes records identified as including the event according to pre-defined logical filters. These pre-defined filters can be clinically derived (e.g., only males have this disease). In the disease example, the result of applying the classification algorithm is a sorted list of individuals suspected of having the disease.

Returning to FIG. 1, in an embodiment of the present invention, the program code integrates the machine learning algorithm into a graphical user interface (170). The graphical user interface enables a user to provide relevant health data and utilizing the interface, the program code can access additional medical information related to the individual. Based on obtaining data through the GUI, the program code applies the constructed classification algorithm to the available data to apply a classification to the individual, based on the data (180). In some embodiments of the present invention, the constructed classification algorithm is a database object that is stored in a memory resource that is communicatively coupled to the processing resource executing the program code. In some embodiments of the present invention, the list produced is a machine-readable data set that is saved by the program code in stored in a memory resource that is communicatively coupled to the processing resource, including but not limited to, a relational database.

In some embodiments of the present invention, the classification is utilized to update the underlying data. In some embodiments of the present invention, the classification is utilized to update the training set and utilized in further analyses. In other embodiments of the present invention, the program code automatically sends a notification to the sources of the records to update the relevant records to record the classification. This message (text, email, etc.) can be sent automatically such that data is shared across sources and the underlying data utilized to train additional data model by the program code includes this generated information. In some embodiments of the present invention, after a given amount of time, a user will update the record of the individual for whom the score was generated by the program code to reflect whether the score was accurate. Based on this adjustment to the accuracy, which can be accomplished through the GUI, the program code can both: 1) adjust the machine learning algorithm; and/or 2) send a notification to the data source(s). As the program code in embodiments of the present invention generates results (scores) and the accuracy of the scores is determined and provided to the program code, the program code can self-learn and continuously tune and improve the machine learning algorithms.

FIG. 2 is an example of a GUI 200 that can be utilized in embodiments of the present invention. This GUI was previously referred to as a Scorecard GUI because it provides a user (e.g., a clinician) with a user-friendly way to classify a user (e.g., patient) based on the constructed classification algorithm. In FIG. 2, the constructed classification algorithm integrated into the GUI is specific to ALS. Based on entry into the GUI 200, one or more programs executed by at least one processor, apply the constructed classification algorithm to the available data to identify records including the event and produce a list of occurrences. The events in this example include symptoms and procedures. Based on the identified records, the program code utilizes the constructed classification algorithm to determine a score, an indicator of a likelihood of a given disease, in this example, ALS. In some embodiments of the present invention, the scorecard is populated automatically based on the program code integrated into the scorecard interfacing with electronic medical records systems. In some embodiments of the present invention, a user enters relevant medical information. Whether or not data is pre-populated, the program code changes the score based upon entry through the GUI 200.

Referring to FIG. 2, a user utilizes the Scorecard GUI 200 generated by the program code to generate a score 210 that indicates to the user whether further action is recommended. As discussed above, certain of the elements in the GUI can be automatically populated by the program code while other elements are entered by a user. In one method of utilizing the GUI, the procedures 220 from the prior history (e.g., 9 to 21 months out) as well as the more recent procedures 230 (e.g., within past 9 months) are automatically populated by the program code in the GUI 200. Meanwhile, in this non-limiting example, the more current drugs 240 (e.g., within past 9 months) and past drugs 250 (e.g., 9 to 21 months out) are populated by the user, as are the current symptoms 260 (e.g., within past 9 months) and past symptoms 270 (e.g., 9 to 21 months out). As the values are populated, the program code adjusts the threshold values 280 and the score 210, progressively. Thus, if a user changes the certain entry value, the effects of the change can be immediately reflected by the program code in the GUI 200. The threshold values 280 can include, but are not limited to, TPR: True Positive Rate, TNR: True Negative Rate, PPV: Positive Predictive Value, FPR: False Positive Rate, AUC: Area Under the Curve. A user can utilize the GUI 200 to make inputs to adjust these values, which would automatically impact the score generated by the program code. In embodiments of the present invention, the field are editable by the user. In some embodiments of the present invention, the user can change the results based on determining, after a time period has lapsed, that the score was incorrect (based on follow up with the patient). The program code obtains this.

FIG. 3 is an example of a GUI 300 that can be utilized in embodiments of the present invention. This GUI 300 was previously referred to as a Scorecard GUI because it provides a user (e.g., a clinician) with a user-friendly way to classify a user (e.g., patient) (there can be different populations that utilize the application) based on the constructed classification algorithm. In FIG. 3, the constructed classification algorithm integrated into the GUI is specific to Hereditary Angioedema (HAE). Based on entry into the GUI 300, one or more programs executed by at least one processors, apply the constructed classification algorithm to the available data to identify records including the event and produce a list of occurrences or events. The events in this example include symptoms (or a diagnosis) (more and less current) 310.320 and procedures (more and less current) 330.340. In this non-limiting example, the less current is general prior history and the more current is within the past year. Based on the identified records, the program code utilizes the constructed classification algorithm to determine a score 350, an indicator of a likelihood of a given disease, in this example, HAE. In some embodiments of the present invention, the scorecard 300 is populated automatically based on the program code integrated into the scorecard interfacing with electronic medical records systems. In some embodiments of the present invention, a user enters relevant medical information. Whether or not data is pre-populated, the program code changes the score 350 (progressively, as a real-time adjustment from the user perspective) based upon entry through the GUI 300. In this HAE-specific example, the scorecard 300 features, both more and less current (e.g., symptoms 310 320, procedures 330 340, drugs 360 370, and provider visits 380 390) are based on the top predictive features used in an underlying algorithm for early identification of HAE patients. The GUI provides an input mechanism for a clinician to collect specific features predictive of HAE exhibited by a patient, then outputs a corresponding HAE score 350 based on the probability of HAE calculated by the underlying algorithm. Aspects of the calculations that are utilized by the program code to generate the score 350 are included as threshold values 395, which are also displayed to the user, through the GUI.

FIG. 4 is an example of a GUI 400 that can be utilized in embodiments of the present invention. In contrast to FIGS. 2-3, FIG. 4 is a more generic example of the Scorecard GUI. The constructed classification algorithm for a given orphan disease and/or other relevant condition is integrated into the GUI. Based on entry into the GUI 400, one or more programs executed by at least one processors, apply the constructed classification algorithm to the available data to identify records including the event and produce a list of occurrences. The events in this example include less and more current symptoms 410 420 and procedures 430 440. The elements that are displayed by the program code (e.g., symptoms, procedure, drugs, provider visits, etc.) are determined by the program code when identifying patterns. Symptoms 410 420 and procedures 430 440 are utilized in FIG. 4 as a non-limiting example, for illustrative purposes only, and do not suggest any limitations. Additionally, the time periods reflected in FIG. 4, prior history and within the past year, are also provided as examples as relevant time periods can be identified by the program code in embodiments of the present invention when identifying patterns. Based on the identified records, the program code utilizes the constructed classification algorithm to determine a score 450, an indicator of a likelihood of a given disease. The user can adjust the disease threshold score for a referral 460, as with the other examples. As with FIGS. 2-3, in some embodiments of the present invention, the scorecard 400 is populated automatically based on the program code integrated into the scorecard interfacing with electronic medical records systems. In some embodiments of the present invention, a user enters relevant medical information. Whether or not data is pre-populated, the program code changes the score based upon entry through the GUI 400. In some embodiments of the present invention, the scorecard 400 is prepopulated and a score 450 is displayed, but as a clinician meets with a patient, the clinician makes adjustments through the GUI 400. Based on the changes made (from information gleaned from the patient interview), the user (clinician) can manually enter data into the GUI 400 and the GUI 400 will dynamically (and progressively) adjust the score 450. In an embodiment of the present invention, a user can also adjust the thresholds for a referral, which will affect the recommendation provided with the score. Examples of scores provided by the scorecard, in some embodiments of the present invention, include: 1) Disease Unlikely—Do Not Refer; 2) Disease Likely—Recommend Test; 3) Disease Likely—Refer to Specialist; and 4) Monitor for Symptom Progression. The word "disease" is used in this example as a stand in for a specific state/event/condition, but depending on the embodiment of the present invention, the program code can provide the name of the specific state/event/condition for which the score is being provided by the program code. In some embodiments of the present invention, the program code matches a specific test with the disease state and/or a specific specialist. In some embodiments of the present invention, if the score exceeds a given threshold, the program code automatically generates a referral or schedules a test. In some embodiments of the present invention, the program code automatically transmits the referral to a specialist (e.g., based on the score "Disease Likely—Refer to Specialist"). The program code can utilize a contact database of specialists to select a specialist based on the score and the related event/condition being identified. In some embodiments of the present invention, the contact information for referrals and the services associated with the referrals can be pre-loaded into a database accessible to the one or more processors executing the program code. In some embodiments of the present invention, the program code interfaces with a scheduling system and automatically schedules and/or requests the scheduling, of a test, based on the score (e.g., Disease Likely—Recommend Test). In some embodiments of the present invention, the program code automatically communicates an action item (or no need to take action) to the medical provider(s) of the patient, based on the score, these action items can include, but are not limited to: do not refer, recommend test, refer to specialist, and monitor for symptom progression.

Figure 6:
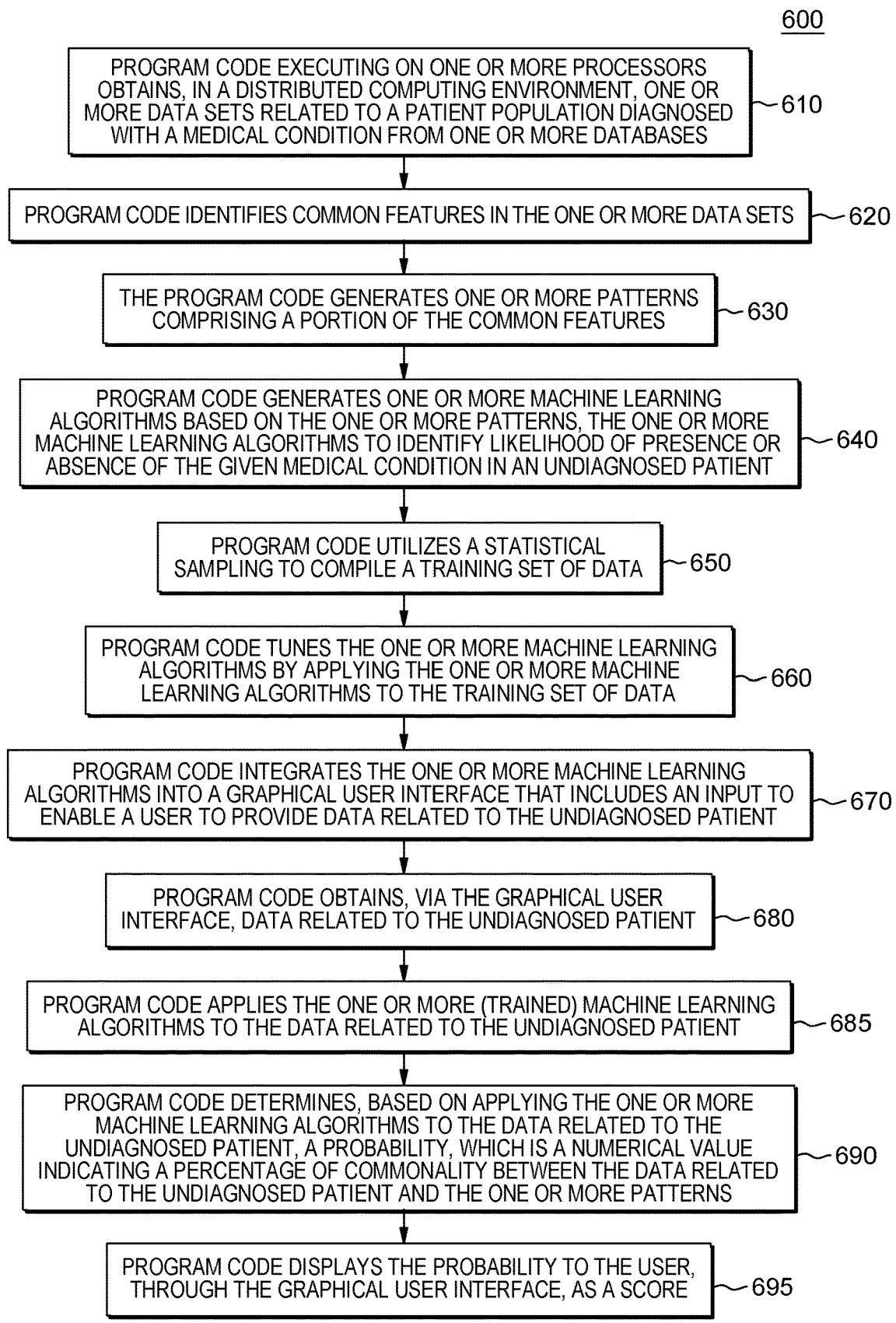
FIG. 6 depicts a workflow associated with aspects of embodiments of the present invention.

FIG. 6 is a workflow 600 that illustrates various aspects of some embodiments of the present invention. In some embodiments of the present invention, program code executing on one or more processors obtains, in a distributed computing environment, one or more data sets related to a patient population diagnosed with a medical condition from one or more databases (610). Based on a frequency of features in the one or more data sets, the program code identifies common features in the one or more data sets (620). The program code generates one or more patterns comprising a portion of the common features (630). The program code generates one or more machine learning algorithms based on the one or more patterns, the one or more machine learning algorithms to identify likelihood of presence or absence of the given medical condition in an undiagnosed patient (640). The program code utilizes a statistical sampling to compile a training set of data (650). The training set can include one or more data sets and at least one additional data set comprising data related to a population without the medical condition. In utilizing the statistical sampling, the program code formulates and obtains queries based on the data set and processing and responds to the queries. The program code tunes the one or more machine learning algorithms by applying the one or more machine learning algorithms to the training set of data (660). The program code integrates the one or more machine learning algorithms into a graphical user interface that includes an input to enable a user to provide data related to the undiagnosed patient (670). In some embodiments of the present invention, the program code generates the graphical user interface and the machine learning algorithms become the logic behind the interface, which is used to evaluate inputs into the interface. In some embodiments of the present invention, the interface is a graphical user interface (GUI) that is generated by program code executing on a content server. The GUI can be a webpage. The program code obtains, via the graphical user interface, data related to the undiagnosed patient (680). The program code applies the one or more (trained) machine learning algorithms to the data related to the undiagnosed patient (685). The program code determines, based on applying the one or more machine learning algorithms to the data related to the undiagnosed patient, a probability, which is a numerical value indicating a percentage of commonality between the data related to the undiagnosed patient and the one or more patterns (690). The program code displays the probability to the user, through the graphical user interface, as a score (695).

Embodiments of the present invention include a computer-implemented method, a computer program product, and a computer system, where program code, executed by one or more processors in a distributed computing environment, obtains one or more data sets related to a patient population diagnosed with a medical condition from one or more databases. Based on a frequency of features in the one or more data sets, the program code identifies common features in the one or more data sets. The program code generates one or more patterns comprising a portion of the common features. The program code generates one or more machine learning algorithms based on the one or more patterns, the one or more machine learning algorithms to identify presence or absence of the given medical condition in an undiagnosed patient. The program code utilizes statistical sampling to compile a training set of data, where the training set comprises data from the one or more data sets and at least one additional data set comprising data related to a population without the medical condition, and where utilizing the statistical sampling comprises formulating and obtaining queries based on the data set and processing and responding to the queries. The program code tunes the one or more machine learning algorithms by applying the one or more machine learning algorithms to the training set of data. The program code integrates the one or more machine learning algorithms into a graphical user interface, where the graphical user interface provides an input to enable a user to provide data related to the undiagnosed patient. The program code obtains data related to the undiagnosed patient. The program code applies the one or more machine learning algorithms to the data related to the undiagnosed patient. The program code determines, based on applying the one or more machine learning algorithms to the data related to the undiagnosed patient, a probability, wherein the probability is a numerical value indicating a percentage of commonality between the data related to the undiagnosed patient and the one or more patterns. The program code displays the probability to the user, through the graphical user interface, as a score.

In some embodiments of the present invention, the program code obtaining the one or more data sets includes: the program code converting the one or more data sets into a standardized format, wherein the formatted data is utilized for the identifying.

In some embodiments of the present invention, a portion of the obtained data is machine readable.

In some embodiments of the present invention, the program code identifies the common features by utilizing a method selected from the group consisting of: weighting the common features based on frequency of occurrence in the one or more data sets, wherein the common features comprise mutual information, performing diffusion mapping, performing principal component analysis, performing recursive feature elimination, and utilizing a Random Forest to select the features.

In some embodiments of the present invention, the program code obtains, via the graphical user interface, additional data related to the undiagnosed patient. The program code applies the one or more machine learning algorithms to the additional data related to the undiagnosed patient. The program code automatically updates, based on applying the one or more machine learning algorithms to the additional data related to the undiagnosed patient, the probability. The program code displays the updated probability to the user, through the graphical user interface, as a score.

In some embodiments of the present invention, the program code determines if the probability exceeds a pre-determined threshold and based on determining that the probability exceeds the pre-determined threshold, the program code automatically transmits the probability to at least one administrator of the one or more databases.

In some embodiments of the present invention, the program code obtains, after a pre-determined period of time, via the graphical user interface, current data related to the undiagnosed patient. The program code determines if the current data is consistent with the probability. Based on the determining, the program code adjusts the one or more machine learning algorithms.

In some embodiments of the present invention, the program code determines if the score meets a predetermined threshold. Based on determining that the score meets the threshold, the program code automatically generates an electronic referral. The program code transmits the electronic referral to a healthcare provider.

Figure 7:
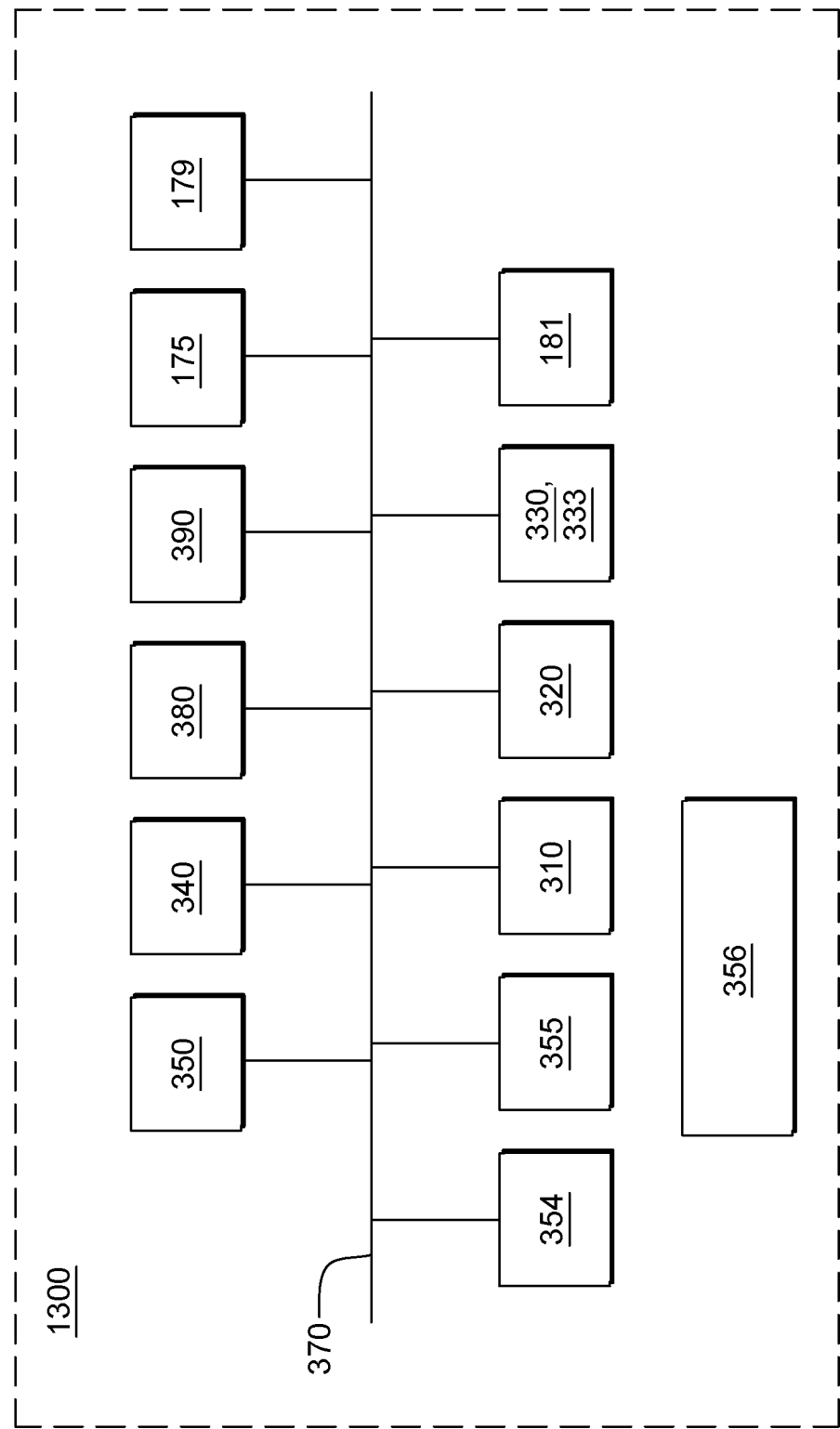
FIG. 7 depicts one embodiment of a single processor computing environment, which can comprise a node of a cloud computing environment, to incorporate and use one or more aspects of the present invention.

FIG. 7 illustrates a block diagram of a resource 1300 in computer system 110 and/or terminal 120a-120b, which is part of the technical architecture of certain embodiments of the technique. As discussed herein, in some embodiments of the present invention, the program code execution is distributed over one or more computing resources, such the illustrated computer system 110. The computer system 110 can also be understood as a node in a cloud computing system upon which aspects of some embodiments of the present invention can be implemented. The resource 1300 can include a circuitry 370 that can in certain embodiments include a microprocessor 354. The computer system 1300 can also include a memory 355 (e.g., a volatile memory device), and storage 181. The storage 181 can include a non-volatile memory device (e.g., EPROM, ROM, PROM, RAM, DRAM, SRAM, flash, firmware, programmable logic, etc.), magnetic disk drive, optical disk drive, tape drive, etc. The storage 355 can comprise an internal storage device, an attached storage device and/or a network accessible storage device. The system 1300 can include a program logic 330 including code 333 that can be loaded into the memory 355 and executed by the microprocessor 356 or circuitry 370.

In certain embodiments, the program logic 330 including code 333 can be stored in the storage 181, or memory 355. In certain other embodiments, the program logic 333 can be implemented in the circuitry 370. Therefore, while FIG. 2 shows the program logic 333 separately from the other elements, the program logic 333 can be implemented in the memory 355 and/or the circuitry 370.

Using the processing resources of a resource 1300 to execute software, computer-readable code or instructions, does not limit where this code can be stored.

Figure 8:
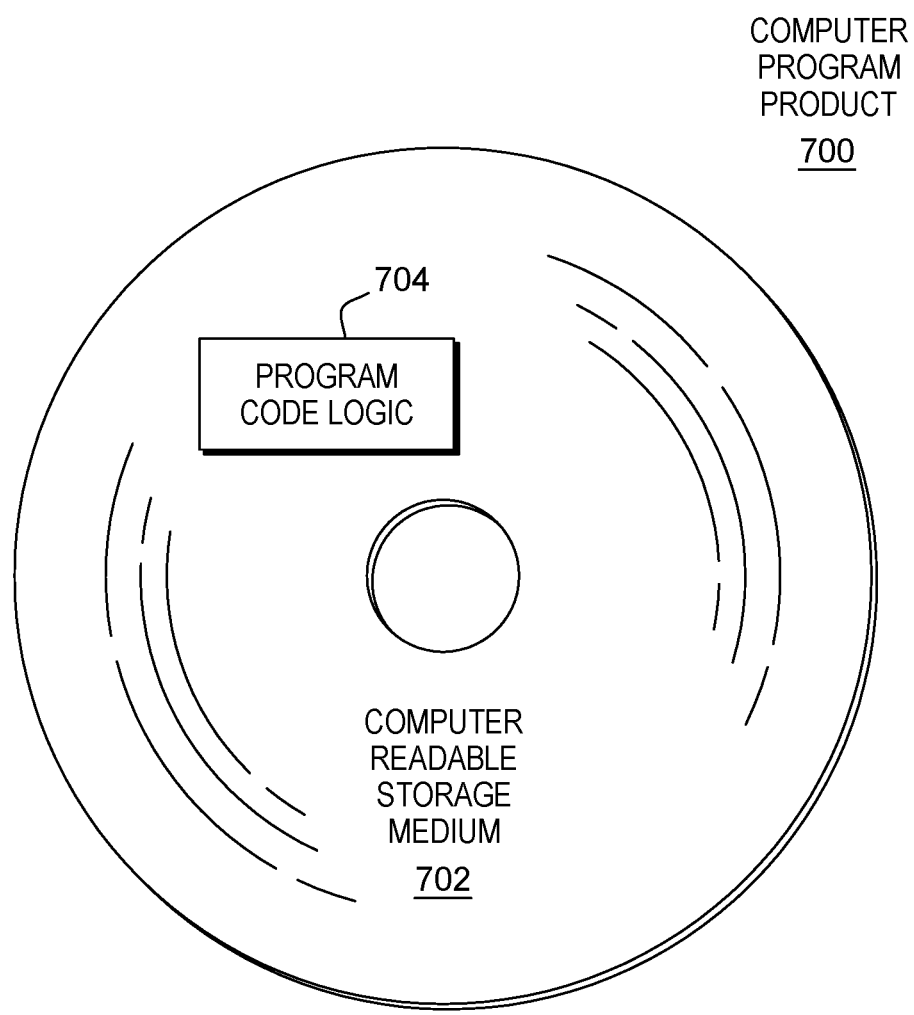
FIG. 8 depicts one embodiment of a computer program product incorporating one or more aspects of the present invention.

Referring to FIG. 8, in one example, a computer program product 700 includes, for instance, one or more non-transitory computer readable storage media 702 to store computer readable program code means or logic 704 thereon to provide and facilitate one or more aspects of the technique.

As will be appreciated by one skilled in the art, aspects of the technique can be embodied as a system, method or computer program product. Accordingly, aspects of the technique can take the form of an entirely hardware embodiment, an entirely software embodiment (including firmware, resident software, micro-code, etc.) or an embodiment combining software and hardware aspects that can all generally be referred to herein as a "circuit," "module" or "system." Furthermore, aspects of the technique can take the form of a computer program product embodied in one or more computer readable medium(s) having computer readable program code embodied thereon.

Any combination of one or more computer readable medium(s) can be utilized. The computer readable medium can be a computer readable signal medium or a computer readable storage medium. A computer readable signal medium can include a propagated data signal with computer readable program code embodied therein, for example, in baseband or as part of a carrier wave. Such a propagated signal can take any of a variety of forms, including, but not limited to, electro-magnetic, optical or any suitable combination thereof. A computer readable signal medium can be any computer readable medium that is not a computer readable storage medium and that can communicate, propagate, or transport a program for use by or in connection with an instruction execution system, apparatus or device.

A computer readable storage medium can be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium can be any tangible medium that can contain or store a program for use by or in connection with an instruction execution system, apparatus, or device.

Program code embodied on a computer readable medium can be transmitted using an appropriate medium, including but not limited to wireless, wireline, optical fiber cable, RF, etc., or any suitable combination of the foregoing.

Computer program code for carrying out operations for aspects of the technique can be written in any combination of one or more programming languages, including an object oriented programming language, such as Java, Smalltalk, Java, Python, R-Language, C++ or the like, and conventional procedural programming languages, such as the "C" programming language, assembler or similar programming languages. The program code can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider).

Aspects of the technique are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions can also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions, also referred to as computer program code, can also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

In addition to the above, one or more aspects of the technique can be provided, offered, deployed, managed, serviced, etc. by a service provider who offers management of customer environments. For instance, the service provider can create, maintain, support, etc. computer code and/or a computer infrastructure that performs one or more aspects of the technique for one or more customers. In return, the service provider can receive payment from the customer under a subscription and/or fee agreement, as examples. Additionally or alternatively, the service provider can receive payment from the sale of advertising content to one or more third parties.

In one aspect of the technique, an application can be deployed for performing one or more aspects of the technique. As one example, the deploying of an application comprises providing computer infrastructure operable to perform one or more aspects of the technique.

As a further aspect of the technique, a computing infrastructure can be deployed comprising integrating computer readable code into a computing system, in which the code in combination with the computing system is capable of performing one or more aspects of the technique. As a further aspect of the technique, the system can operate in a peer to peer mode where certain system resources, including but not limited to, one or more databases, is/are shared, but the program code executable by one or more processors is loaded locally on each computer (workstation).

As yet a further aspect of the technique, a process for integrating computing infrastructure comprising integrating computer readable code into a computer system can be provided. The computer system comprises a computer readable medium, in which the computer medium comprises one or more aspects of the technique. The code in combination with the computer system is capable of performing one or more aspects of the technique.

Further, other types of computing environments can benefit from one or more aspects of the technique. As an example, an environment can include an emulator (e.g., software or other emulation mechanisms), in which a particular architecture (including, for instance, instruction execution, architected functions, such as address translation, and architected registers) or a subset thereof is emulated (e.g., on a native computer system having a processor and memory). In such an environment, one or more emulation functions of the emulator can implement one or more aspects of the technique, even though a computer executing the emulator can have a different architecture than the capabilities being emulated. As one example, in emulation mode, the specific instruction or operation being emulated is decoded, and an appropriate emulation function is built to implement the individual instruction or operation.

In an emulation environment, a host computer includes, for instance, a memory to store instructions and data; an instruction fetch unit to fetch instructions from memory and to optionally, provide local buffering for the fetched instruction; an instruction decode unit to receive the fetched instructions and to determine the type of instructions that have been fetched; and an instruction execution unit to execute the instructions. Execution can include loading data into a register from memory; storing data back to memory from a register; or performing some type of arithmetic or logical operation, as determined by the decode unit. In one example, each unit is implemented in software. For instance, the operations being performed by the units are implemented as one or more subroutines within emulator software.

Further, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters can also be coupled to the system to enable the data processing system to become coupled to other data processing systems or remote printers or storage devices through intervening private or public networks. Modems, cable modems, and Ethernet cards are just a few of the available types of network adapters.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the descriptions below, if any, are intended to include any structure, material, or act for performing the function in combination with other elements as specifically noted. The description of the technique has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer-implemented method, comprising:
   obtaining, by one or more processors in a distributed computing environment, one or more data sets related to a patient population diagnosed with a medical condition from one or more databases;
   based on a frequency of features in the one or more data sets, identifying, by the one or more processors, common features in the one or more data sets and weighting the common features based on frequency of occurrence in the portion of the data, wherein the common features comprise mutual information;
   utilizing, by the one or more processors, the mutual information to generate a patient definition, wherein generating the patient definition comprises:
   truncating, by the one or more processors, the common features based on identifying one or more common features of the common features with mutual information values above a predefined threshold, wherein the mutual information value for each common feature of the common features comprises a weighted value for the common feature based on the frequency of occurrence of the common feature in the portion of the data, wherein the truncating comprises ranking the weighted values and selecting one or more common features from the common features wherein the selected common features comprise the one or more features with the mutual information values above the predefined threshold; and
   selecting, by the one or more processors, from the one or more common features with the mutual information values above the predefined threshold, a portion of the common features, wherein the portion of the common features comprises a smallest subset of common features from the one or more common features with the mutual information values above the predefined threshold comprising a majority of common features of the one or more features with the mutual information values above the predefined threshold, wherein the portion of the common features comprises the patient definition;
   generating, by the one or more processors, one or more machine learning algorithms based on the patient definition, the one or more machine learning algorithms to identify presence or absence of the given medical condition in an undiagnosed patient;
   utilizing, by the one or more processors, statistical sampling to compile a training set of data, wherein the training set comprises data from the one or more data sets and at least one additional data set comprising data related to a population without the medical condition, and wherein utilizing the statistical sampling comprises formulating and obtaining queries based on the training data and processing and responding to the queries;
   tuning, by the one or more processors, the one or more machine learning algorithms by applying the one or more machine learning algorithms to the training set of data;
   integrating, by the one or more processors, the one or more machine learning algorithms into a graphical user interface, wherein the graphical user interface provides an input to enable a user to provide data related to the undiagnosed patient;
   obtaining, by the one or more processors, via the graphical user interface, data related to the undiagnosed patient;
   applying, by the one or more processors, the one or more machine learning algorithms to the data related to the undiagnosed patient;
   determining, by the one or more processors, based on applying the one or more machine learning algorithms to the data related to the undiagnosed patient, a probability, wherein the probability is a numerical value indicating a percentage of commonality between the data related to the undiagnosed patient and the patient definition; and displaying, by the one or more processors, the probability to the user, through the graphical user interface, as a score.

2. The computer-implemented method of claim 1, wherein obtaining the one or more data sets comprises:
converting, by the one or more processors, the one or more data sets into a standardized format, wherein the formatted data is utilized for the identifying.

3. The computer-implemented method of claim 2, wherein a portion of the obtained data is machine readable.

4. The computer-implemented method of claim 1, wherein identifying the common features is performed utilizing a method selected from the group consisting of: weighting the common features based on frequency of occurrence in the one or more data sets, wherein the common features comprise mutual information, performing diffusion mapping, performing principal component analysis, performing recursive feature elimination, and utilizing a Random Forest to select the features.

5. The computer-implemented method of claim 1, further comprising:
obtaining, by the one or more processors, via the graphical user interface, additional data related to the undiagnosed patient;
applying, by the one or more processors, the one or more machine learning algorithms to the additional data related to the undiagnosed patient;
automatically updating, by the one or more processors, based on applying the one or more machine learning algorithms to the additional data related to the undiagnosed patient, the probability; and
displaying, by the one or more processors, the updated probability to the user, through the graphical user interface, as a score.

6. The computer-implemented method of claim 1, further comprising:
determining, by the one or more processors, if the probability exceeds a pre-determined threshold; and
based on determining that the probability exceeds the pre-determined threshold, automatically transmitting, by the one or more processors, the probability to at least one administrator of the one or more databases.

7. The computer-implemented method of claim 1, further comprising:
obtaining, by the one or more processors, after a pre-determined period of time, via the graphical user interface, current data related to the undiagnosed patient;
determining, by the one or more processors, if the current data is consistent with the probability; and
based on the determining, adjusting, by the one or more processors, the one or more machine learning algorithms.

8. The computer-implemented method of claim 1, further comprising determining by the one or more processors, if the score meets a predetermined threshold;
based on determining that the score meets the threshold, automatically generating, by the one or more processors, an electronic referral; and
transmitting, by the one or more processors, the electronic referral to a healthcare provider.

9. A computer program product comprising:
a computer readable storage medium readable by one or more processors in a distributed computing environment, and storing instructions for execution by the one or more processors for performing a method comprising:

obtaining, by the one or more processors in a distributed computing environment, one or more data sets related to a patient population diagnosed with a medical condition from one or more databases;
based on a frequency of features in the one or more data sets, identifying, by the one or more processors, common features in the one or more data sets and weighting the common features based on frequency of occurrence in the portion of the data, wherein the common features comprise mutual information;
utilizing, by the one or more processors, the mutual information to generate a patient definition, wherein generating the patient definition comprises:
truncating, by the one or more processors, the common features based on identifying one or more common features of the common features with mutual information values above a predefined threshold, wherein the mutual information value for each common feature of the common features comprises a weighted value for the common feature based on the frequency of occurrence of the common feature in the portion of the data, wherein the truncating comprises ranking the weighted values and selecting one or more common features from the common features wherein the selected common features comprise the one or more features with the mutual information values above the predefined threshold; and
selecting, by the one or more processors, from the one or more common features with the mutual information values above the predefined threshold, a portion of the common features, wherein the portion of the common features comprises a smallest subset of common features from the one or more common features with the mutual information values above the predefined threshold comprising a majority of common features of the one or more features with the mutual information values above the predefined threshold, wherein the portion of the common features comprises the patient definition;
generating, by the one or more processors, one or more machine learning algorithms based on the patient definition, the one or more machine learning algorithms to identify presence or absence of the given medical condition in an undiagnosed patient;
utilizing, by the one or more processors, statistical sampling to compile a training set of data, wherein the training set comprises data from the one or more data sets and at least one additional data set comprising data related to a population without the medical condition, and wherein utilizing the statistical sampling comprises formulating and obtaining queries based on the training data and processing and responding to the queries;
tuning, by the one or more processors, the one or more machine learning algorithms by applying the one or more machine learning algorithms to the training set of data;
integrating, by the one or more processors, the one or more machine learning algorithms into a graphical user interface, wherein the graphical user interface provides an input to enable a user to provide data related to the undiagnosed patient;
obtaining, by the one or more processors, via the graphical user interface, data related to the undiagnosed patient;
applying, by the one or more processors, the one or more machine learning algorithms to the data related to the undiagnosed patient;

determining, by the one or more processors, based on applying the one or more machine learning algorithms to the data related to the undiagnosed patient, a probability, wherein the probability is a numerical value indicating a percentage of commonality between the data related to the undiagnosed patient and the patient definition; and displaying, by the one or more processors, the probability to the user, through the graphical user interface, as a score.

10. The computer program product of claim 9, wherein obtaining the one or more data sets comprises:

converting, by the one or more processors, the one or more data sets into a standardized format, wherein the formatted data is utilized for the identifying.

11. The computer program product of claim 10, wherein a portion of the obtained data is machine readable.

12. The computer program product of claim 9, wherein identifying the common features is performed utilizing a method selected from the group consisting of: weighting the common features based on frequency of occurrence in the one or more data sets, wherein the common features comprise mutual information, performing diffusion mapping, performing principal component analysis, performing recursive feature elimination, and utilizing a Random Forest to select the features.

13. The computer program product of claim 9, further comprising:

obtaining, by the one or more processors, via the graphical user interface, additional data related to the undiagnosed patient;

applying, by the one or more processors, the one or more machine learning algorithms to the additional data related to the undiagnosed patient;

automatically updating, by the one or more processors, based on applying the one or more machine learning algorithms to the additional data related to the undiagnosed patient, the probability; and displaying, by the one or more processors, the updated probability to the user, through the graphical user interface, as a score.

14. The computer program product of claim 9, further comprising:

determining, by the one or more processors, if the probability exceeds a pre-determined threshold; and based on determining that the probability exceeds the pre-determined threshold, automatically transmitting, by the one or more processors, the probability to at least one administrator of the one or more databases.

15. The computer program product of claim 9, further comprising:

obtaining, by the one or more processors, after a pre-determined period of time, via the graphical user interface, current data related to the undiagnosed patient;

determining, by the one or more processors, if the current data is consistent with the probability; and based on the determining, adjusting, by the one or more processors, the one or more machine learning algorithms.

16. The computer program product of claim 9, further comprising determining by the one or more processors, if the score meets a predetermined threshold;

based on determining that the score meets the threshold, automatically generating, by the one or more processors, an electronic referral; and transmitting, by the one or more processors, the electronic referral to a healthcare provider.

17. A system comprising:

one or more memory;

one or more processors in communication with the memory; and program instructions executable by the one or more processors in a distributed computed environment via the one or more memory to perform a method, the method comprising: obtaining, by the one or more processors in a distributed computing environment, one or more data sets related to a patient population diagnosed with a medical condition from one or more databases;

based on a frequency of features in the one or more data sets, identifying, by the one or more processors, common features in the one or more data sets and weighting the common features based on frequency of occurrence in the portion of the data, wherein the common features comprise mutual information;

utilizing, by the one or more processors, the mutual information to generate a patient definition, wherein generating the patient definition comprises:

truncating, by the one or more processors, the common features based on identifying one or more common features of the common features with mutual information values above a predefined threshold, wherein the mutual information value for each common feature of the common features comprises a weighted value for the common feature based on the frequency of occurrence of the common feature in the portion of the data, wherein the truncating comprises ranking the weighted values and selecting one or more common features from the common features wherein the selected common features comprise the one or more features with the mutual information values above the predefined threshold; and selecting, by the one or more processors, from the one or more common features with the mutual information values above the predefined threshold, a portion of the common features, wherein the portion of the common features comprises a smallest subset of common features from the one or more common features with the mutual information values above the predefined threshold comprising a majority of common features of the one or more features with the mutual information values above the predefined threshold, wherein the portion of the common features comprises the patient definition;

generating, by the one or more processors, one or more machine learning algorithms based on the patient definition, the one or more machine learning algorithms to identify presence or absence of the given medical condition in an undiagnosed patient;

utilizing, by the one or more processors, statistical sampling to compile a training set of data, wherein the training set comprises data from the one or more data sets and at least one additional data set comprising data related to a population without the medical condition, and wherein utilizing the statistical sampling comprises formulating and obtaining queries based on the training data and processing and responding to the queries;

tuning, by the one or more processors, the one or more machine learning algorithms by applying the one or more machine learning algorithms to the training set of data;

integrating, by the one or more processors, the one or more machine learning algorithms into a graphical user interface, wherein the graphical user interface provides an input to enable a user to provide data related to the undiagnosed patient;

obtaining, by the one or more processors, via the graphical user interface, data related to the undiagnosed patient;

applying, by the one or more processors, the one or more machine learning algorithms to the data related to the undiagnosed patient;

determining, by the one or more processors, based on applying the one or more machine learning algorithms to the data related to the undiagnosed patient, a probability, wherein the probability is a numerical value indicating a percentage of commonality between the data related to the undiagnosed patient and the patient definition; and displaying, by the one or more processors, the probability to the user, through the graphical user interface, as a score.

18. The system of claim 17, wherein obtaining the one or more data sets comprises:

converting, by the one or more processors, the one or more data sets into a standardized format, wherein the formatted data is utilized for the identifying.

19. The system of claim 18, wherein a portion of the obtained data is machine readable.

20. The system of claim 17, wherein identifying the common features is performed utilizing a method selected from the group consisting of: weighting the common features based on frequency of occurrence in the one or more data sets, performing diffusion mapping, performing principal component analysis, performing recursive feature elimination, and utilizing a Random Forest to select the features.

* * * * *